(12) United States Patent
Needham et al.

(10) Patent No.: US 10,996,221 B2
(45) Date of Patent: May 4, 2021

(54) MULTIPLEXED LATERAL FLOW ASSAY SYSTEMS AND METHODS FOR THEIR USE

(71) Applicant: InBios International, Inc., Seattle, WA (US)

(72) Inventors: James William Needham, Seattle, WA (US); Syamal Raychaudhuri, Seattle, WA (US)

(73) Assignee: InBios International, Inc., Seattle, WA (US)

( * ) Notice: Subject to any disclaimer, the term of this patent is extended or adjusted under 35 U.S.C. 154(b) by 620 days.

(21) Appl. No.: 15/491,825

(22) Filed: Apr. 19, 2017

(65) Prior Publication Data

US 2017/0219573 A1 Aug. 3, 2017

Related U.S. Application Data

(63) Continuation-in-part of application No. PCT/US2016/057150, filed on Oct. 14, 2016.

(Continued)

(51) Int. Cl.
*G01N 33/558* (2006.01)
*B01L 3/00* (2006.01)
(Continued)

(52) U.S. Cl.
CPC .......... *G01N 33/558* (2013.01); *B01L 3/5023* (2013.01); *G01N 33/54346* (2013.01); *G01N 33/54386* (2013.01); *G01N 33/56911* (2013.01); *G01N 33/56916* (2013.01); *G01N 33/56922* (2013.01); *G01N 33/56983* (2013.01); *B01L 2200/028* (2013.01); *B01L 2200/0621* (2013.01); *B01L 2300/0681* (2013.01);
(Continued)

(58) Field of Classification Search
USPC ..... 422/400, 401, 420, 425, 430; 435/287.7, 435/287.9, 970, 805, 810, 973; 436/169, 436/514, 518, 524, 530, 810
See application file for complete search history.

(56) References Cited

U.S. PATENT DOCUMENTS 4,313,734 A 2/1982 Leuvering
4,376,110 A 3/1983 David et al.
(Continued)

FOREIGN PATENT DOCUMENTS

WO 97/31268 A1 8/1997
WO 2011/051562 A1 5/2011
(Continued)

OTHER PUBLICATIONS

Cimaglia et al., "Quantum dots nanoparticle-based lateral flow assay for rapid detection of *Mycobacterium* species using anti-FprA antibodies," *Nanotechnology Development* 2(5):26-30, 2012.
(Continued)

*Primary Examiner* — Christopher L Chin
(74) *Attorney, Agent, or Firm* — Seed IP Law Group LLP

(57) ABSTRACT

A device for performing a multiplex lateral flow immunoassay is provided in which a liquid sample, such as a biological sample, is simultaneously tested for the presence of multiple analytes of interest. Methods that employ the device in the simultaneous detection of multiple analytes of interest within a liquid test sample are also provided.

34 Claims, 7 Drawing Sheets

Related U.S. Application Data

(60) Provisional application No. 62/242,213, filed on Oct. 15, 2015.

(51) Int. Cl.
*G01N 33/543* (2006.01)
*G01N 33/569* (2006.01)

(52) U.S. Cl.
CPC .................. *B01L 2300/0825* (2013.01); *B01L 2300/0864* (2013.01); *B01L 2400/0406* (2013.01); *G01N 2800/26* (2013.01); *Y02A 50/30* (2018.01)

(56) References Cited

U.S. PATENT DOCUMENTS

| | | | |
|---|---|---|---|
| 4,435,504 A | | 3/1984 | Zuk et al. |
| 4,703,017 A | | 10/1987 | Campbell et al. |
| 4,855,240 A | | 8/1989 | Rosenstein et al. |
| 4,954,452 A | | 9/1990 | Yost et al. |
| 5,028,535 A | | 7/1991 | Buechler et al. |
| 5,075,078 A | | 12/1991 | Osikowicz et al. |
| 5,238,652 A | * | 8/1993 | Sun ..................... B01L 3/5027 422/412 |
| 5,252,496 A | * | 10/1993 | Kang ............... G01N 33/54366 436/529 |
| 5,602,040 A | * | 2/1997 | May ................ G01N 33/54366 422/401 |
| 5,707,818 A | * | 1/1998 | Chudzik .......... G01N 33/54366 422/412 |
| 5,972,720 A | * | 10/1999 | Nichtl ................. G01N 33/553 435/40.52 |
| 8,580,572 B2 | | 11/2013 | Lappalainen |
| 8,846,319 B2 | | 9/2014 | Mehra et al. |
| 8,945,838 B2 | | 2/2015 | Heemstra |
| 9,034,656 B2 | | 5/2015 | Mehra et al. |
| 2007/0105237 A1 | | 5/2007 | Corstjens et al. |
| 2007/0224701 A1 | | 9/2007 | Rosenstein |
| 2007/0248983 A1 | | 10/2007 | Schwind et al. |
| 2010/0159599 A1 | | 4/2010 | Song et al. |
| 2012/0015350 A1 | | 1/2012 | Nabatiyan et al. |
| 2012/0040336 A1 | | 2/2012 | Bisgrove et al. |
| 2012/0184462 A1 | | 7/2012 | O'Farrell et al. |
| 2012/0220049 A1 | | 8/2012 | Bunce et al. |
| 2013/0017561 A1 | | 1/2013 | Marr et al. |
| 2013/0022969 A1 | | 1/2013 | Kim et al. |
| 2013/0280698 A1 | | 10/2013 | Propper et al. |
| 2014/0093865 A1 | | 4/2014 | Espinosa et al. |
| 2015/0086974 A1 | | 3/2015 | Yoshida et al. |

FOREIGN PATENT DOCUMENTS

| | | |
|---|---|---|
| WO | 2014/184151 A1 | 11/2014 |
| WO | 2015/008287 A1 | 1/2015 |

OTHER PUBLICATIONS

Hayat (ed), *Colloidal Gold*, vol. 1, Academic Press Inc., Harcourt Brace Jovanovich, San Diego, California, 1989, 566 pages.

Juntunen et al., "Performance of fluorescent europium(III) nanoparticles and colloidal gold reporters in lateral flow bioaffinity assay," *Analytical Biochemistry* 428(1):31-38, 2012 (abstract), 3 pages.

Mansfield, "Design Considerations for Lateral Flow Test Strips," PowerPoint presentation, *EMD Millipore*, 32 pages, 2015.

Sajid et al., "Designs, formats and applications of lateral flow assay: A literature review," *Journal of Saudi Chemical Society* 19:689-705, 2015.

Soloviev (ed), *Nanoparticles in Biology and Medicine: Methods and Protocols*, vol. 906, Humana Press, New York, New York, 2012, Chapter 4, pp. 45-52, Bailes et al., "Gold Nanoparticle Antibody Conjugates for Use in Competitive Lateral Flow Assays," 11 pages.

Swanson et al., "Lateral Flow Assay with Near-Infrared Dye for Multiplex Detection," *Clinical Chemistry* 59(4):641-648, 2013.

Xu et al., "Fluorescent Probe-Based Lateral Flow Assay for Multiplex Nucleic Acid Detection," *Analytical Chemistry* 86(12):5611-5614, 2014 (abstract), 2 pages.

\* cited by examiner

MULTIPLEXED LATERAL FLOW ASSAY SYSTEMS AND METHODS FOR THEIR USE

CROSS-REFERENCE TO RELATED APPLICATIONS

This application is a continuation-in-part of International Application No. PCT/US2016/057150, filed Oct. 14, 2016, which claims the benefit under 35 U.S.C. § 119(e) of U.S. Provisional Patent Application No. 62/242,213 filed Oct. 15, 2015, where each application is incorporated herein by reference in its entirety for all purposes.

FIELD OF THE INVENTION

The present invention relates generally to systems and methods for assaying analytes, such as ligands, within a fluid sample. More specifically, the invention relates to the use of a multiplexed lateral low device to determine the presence and/or amount of multiple analytes simultaneously in a biological sample.

BACKGROUND

Lateral flow immunoassays, also called lateral flow tests, dipsticks or simply strip tests, are simple one- or two-step assays for the qualitative determination of analytes directly in liquid samples. Specific lines, or zones, are "striped" onto, or applied to, a test membrane that contains capture reagents designed to react with and bind to predefined analytes of interest that may be present in a liquid test sample. When a liquid sample is applied to one end of the test membrane, the sample is drawn by capillary action along the longitudinal axis of the membrane strip. Analytes of interest present in the sample interact with the capture reagents, producing measurable and detectable changes along the striped analyte assay test zones. The benefits of lateral flow tests include: (a) they have a user-friendly format; (b) a very short time is required to obtain the test result; (c) they have long-term stability over a wide range of climates; and (d) they are relatively inexpensive to make. These features make strip tests ideal for applications such as home testing, rapid point-of-care testing, and testing in the field for various environmental and agricultural analytes. In addition, they provide reliable testing that might not otherwise be available in developing countries.

A rapid lateral flow test generally consists of a system of overlapping porous materials containing the dried components needed to perform the test. These membranes are assembled in small strips, which can be placed into a plastic housing for ease in handling. Lateral flow tests can be used to detect any ligand that can be bound to a visually detectable capture reagent attached to a solid support, both qualitatively and, in many cases, semi-quantitatively. Some of the more common lateral flow tests currently on the market are those for pregnancy, strep throat and Chlamydia infection. For these conditions a quantitative assay is not necessary.

A typical prior art lateral flow assay format is shown in FIG. 1. The sample to be tested, such as a biological sample, is loaded onto sample application pad 10. In the case of whole blood or capillary blood samples, separation of blood cells and plasma takes place on sample pad 10. The sample application pad 10 is typically adhered to a rigid or semi-rigid backing card 11. For example, the sample pad 10 may be laminated to a mylar support film which functions as the backing card 11. The liquid fraction of the sample then moves through a conjugate release pad 12 onto which a conjugate has been dried. The conjugate consists of detection molecules specifically directed against the analyte of interest and indicator particles, such as colloidal gold or gold sol. Upon contact with the liquid sample, the conjugate redissolves and specifically binds to any analyte present in the sample to form an analyte-conjugate complex. In certain formats a liquid conjugate, such as a liquid gold conjugate, is employed and the conjugate pad is omitted (see U.S. Pat. No. 8,399,261).

The analyte-conjugate complex flows through a capillary membrane 14, such as a nitrocellulose membrane (also referred to as the analytical membrane), on which test and control reagents have been immobilized. More specifically, membrane 14 is provided with two capture lines, or regions, arranged sequentially and positioned perpendicularly to the flow direction theta ($\Theta$), each containing bound reagents. Test line 16 contains analyte-specific molecules which are able to bind to and immobilize the analyte-conjugate complex, resulting in a visible colored line. Control line 18 does not contain analyte-specific molecules but is able to fix non-bound conjugate-containing particles. The formation of a colored line at control line 18 indicates that the test sample has flowed past test line 16. The color intensity observed at test line 16 is directly proportional to the analyte concentration in the sample and therefore enables semi-quantitative interpretation of the test result. If the analyte of interest is present at a level above the detection limit, test line 16 and control line 18 both become clearly visible. If the analyte is present at a level below the detection limit, only control line 18 becomes visible during the test The last component of the rapid test device is an absorbent pad 20 (also known as a wicking or sink pad) which collects the fluid flowing through the test system and prevents any backflow of fluid. Absorbent pad 20 allows the use of samples whose volume exceeds the wicking capacity of nitrocellulose membrane 14.

Traditional lateral flow immunoassays are designed to detect and measure a single analyte per test device and therefore detection of multiple analytes in a single sample can only be performed sequentially. While such tests are well-established and validated techniques, they can be time-consuming, sample-depleting and costly when employed to measure numerous analytes per sample. Bead-based immunoassays utilize the same principle as strip tests but employ uniquely identifiable beads. These beads enable simultaneous detection of multiple analytes in a single well or reaction but generally require the use of expensive equipment to read the results and are thus not suitable for point-of-care or field use. In alternative methods, reagents that are specific for multiple different analytes are positioned at specific locations in an array (for example in pre-designated wells of a 96-well plate) and portions of a test sample are added to each of the wells. Again, these methods are less effective for point-of-care or field use than conventional dipstick tests.

Other multiplexed lateral flow assay systems align multiple lateral flow assays, or test strips, into a single large cassette. A liquid test sample is applied at a specific location and then divided and directed into multiple separate channels, with each channel containing agents for detecting a specific analyte. For example, US 2013/0280698 discloses a multi-strip assay cartridge in which multiple lateral flow assay strips are located within a single housing. A liquid test sample is introduced into a diversion dam via an inlet in the housing and subsequently split between multiple flow channels, each flow channel being connected to a separate assay chamber that contains components necessary for detection of a single analyte. Similarly, U.S. Pat. No. 8,715,590 discloses a cross-flow analyte assay array in which one or more test samples are introduced through at least one test sample input application port and distributed through multiple fluid flow manifolds to multiple fluid flow channels positioned in parallel rows that are located perpendicular or transverse to the longitudinal direction of fluid flow. Such devices are more complex, and therefore more expensive, to produce than standard dipstick tests.

Other descriptions of lateral flow assay devices may be found in, e.g., Sajid M. et al. Journal of Saudi Chemical Society (2015) v. 19 pp. 689-705 and references cited therein; "Design Considerations for Lateral Flow Test Strips" pp. 1-32, presentation by Michael A. Mansfield, 24 Jun. 2015; "Rapid Lateral Flow Test Strips, Considerations for Product Development" pp. 1-39, copyright 2002, 2008 by Millipore Corporation, Billerica, Mass., available at the website millipore.com/diagnostics. See also U.S. Pat. Nos. 4,313,734, 4,376,110, 4,435,504, 4,703,017, 4,855,240, 4,954,452, 5,028,535, 5,075,078, 8,580,572, 8,846,319, 8,945,838, 9,034,656, and U.S. Patent Publication Nos. 2015/086974, 2014/0093865, 2013/0017561, 2013/0022969, 2013/0280698, 2012/0040336, 2012/0015350 and 2010/0159599. See also, e.g., PCT Publication Nos. WO2014/184151 and WO2011/051562.

There thus remains a need in the art for a multiplexed lateral flow assay system with high specificity and sensitivity that is relatively inexpensive to produce and that is both easy to use and stable under a variety of environmental conditions.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

The present disclosure provides a device for performing a multiplex lateral flow immunoassay in which a liquid sample, such as a biological sample, is simultaneously tested for the presence of multiple analytes of interest. Methods that employ the device in the simultaneous detection of multiple analytes of interest within a liquid test sample are also provided.

The devices and methods disclosed herein can be employed to detect the presence of analytes that are indicative of the presence of disorders or conditions such as infectious diseases, pregnancy, microbial infections, cancer, autoimmune disorders, cardiac disorders, allergic disorders, drug abuse, and the like. Infectious diseases that can be detected using the disclosed devices and methods include, but are not limited to: fever causing agents including malaria, scrub typhus, rickettsia, typhoid fever, dengue, and chikungunya; biological select agents such as, but not limited to, melioidosis, anthrax, and plague; leishmaniasis; tuberculosis; syphilis; Chagas disease; encephalitis; leprosy; West Nile virus; Shigella, *Campylobacter*; and enterotoxigenic *E. coli*. Analytes that can be detected using the disclosed device and methods include, but are not limited to, proteins and/or peptides, including ligands and receptors; non-protein molecules, such as carbohydrates, phospholipids and nucleic acids; small molecules; and other molecules of biological interest.

In one embodiment, the device described herein comprises at least two assay test paths with each assay test path containing a capture reagent (such as an antibody or antigen) specific for a specific analyte of interest that is sprayed onto a single analytical membrane, such as a nitrocellulose membrane. Additionally on the single analytical membrane, detection reagents specific for the analytes of interest (such as an antibody or antigen) labeled with a reporter agent are spotted/dried in precise locations along the at least two assay test paths, with each assay test path containing at least one labeled detection reagent specific for an analyte. Each assay test path thus contains the components necessary for detecting the presence or absence of a single specific analyte. The reporter agent may be any suitable reporter agent known to those of skill in the art, for example, colloidal nanoparticles, latex microspheres, quantum dots, enzymes, fluorophores and the like, provided that the labeled detection reagent possesses a low diffusion constant, D (with an effective membrane diffusion constant of typically $D_{\mathit{eff}} < 10^{-8}$ m$^2$/sec.). Additionally, the assay is constructed such that the flow of the liquid test sample (i.e., the effective velocity of the solution) through the membrane is approximately uniform across the lateral axis of the assay by ensuring that the liquid sample is uniformly distributed prior to entering the membrane. This is most readily achieved by permitting the sample to wet through a sample pad or treated glass fiber pad that rapidly takes up volume to that the liquid sample can enter into the membrane as uniformly as possible. Thus, in one embodiment, the sample travels the same distance in moving from the sample pad to the detection reagent in the first assay test path as it does in moving from the sample pad to the detection reagent in the second assay test path. When the sample travels the same distance, i.e., has the same path length, under the same conditions so that it simultaneously reaches the detection reagents in the first and second (and optionally, third, fourth, fifth, sixth, etc.) assay test paths, the device of the present disclosure may achieve concurrent detection of analytes.

Upon addition of a liquid test sample, the dried labeled detector particles are solubilized and flow uniformly along the longitudinal axis of the assay. As a result of the low diffusion constant of the labeled detection reagents, the lateral diffusion of the particles is very limited and thus, due to the fluid mechanics of the system, specific lanes, or test paths, of labeled detector particles are created such that each test path indicates the presence or absence of an individual analyte in the test sample.

One or more spots of labeled detection reagents can be present in any given test path such that the number of analytes detected in the assay can be further multiplied. In such a manner, a very large number of analytes can be evaluated from a single test sample using a very small footprint. A single sample entry application port is used to apply the liquid test sample. A separate buffer port can optionally be present in order to ensure proper flow of the immunoassay. No barrier, e.g., no physical or chemical barrier, is necessarily provided between the multiple assay test paths in order to provide physical lanes for multiplexing the assay. In one embodiment, when a line is drawn perpendicular to two adjacent assay test paths, that line does not cross a barrier, e.g., not a physical barrier such as a wall, or a chemical barrier such as a hydrophobic, i.e., water repelling, region.

In addition, multiple spots of labeled detection reagents can be present in any given assay test path, thereby having a multiplicative effect on the number of analytes that can be detected in a single test sample. As a result, the present disclosure provides a very dense, easy to produce, multiplexed assay within a very small device footprint.

In addition, as no physical barrier is necessary to create the multiplexed assay test paths, the assay can be performed in a "dipstick" format (i.e., without a plastic housing or enclosure) as no enclosure is necessary to perform the multiplexed assay, further reducing manufacturing costs. In some embodiments, the capture reagents on the membrane are not necessarily "spotted" in order to localize the assay reaction (although they may be), but rather are "striped" across the membrane, significantly increasing the ease-of-manufacturing. Due to the lack of diffusion along the test paths, however, an array indicating the presence of the variety of analytes is still generated upon the addition of the test sample.

In a specific embodiment, a multiplex lateral flow assay device for simultaneous detection of a presence of at least a first analyte of interest and a second, different, analyte of interest in a single liquid test sample is provided, the device comprising: (a) a test sample receiving region; and (b) a capture membrane comprising a first assay test path and a second, adjacent, assay test path, the first assay test path comprising a first labeled detection reagent specific for the first analyte of interest, and a first test line comprising an immobilized first capture reagent specific for the first analyte of interest, and the second assay test path comprising a second, different, labeled detection reagent specific for the second analyte of interest, and a second test line comprising an immobilized second, different, capture reagent specific for the second analyte of interest, wherein each of the first and second labeled detection reagents has a low diffusion constant such that there is little to no lateral diffusion of the first and second labeled detection reagents between the first and second assay test paths following solubilization by the liquid test sample. Because there is little to no lateral diffusion of sample as it travels along an assay test path, there is no need to place a barrier between the assay test paths, i.e., the multiple assay test paths may be located within a single assay chamber. Furthermore, the multiple assay test paths may be placed on a single piece of capture membrane, i.e., a continuous piece of capture membrane. In certain embodiments, the device further comprises a control line positioned downstream of the first and second test lines, the control line comprising an immobilized control reagent that binds to the first and second labeled detection reagents.

While the present disclosure provides test strips and devices that comprise a plurality of assay test paths, the present disclosure also provides test strips and devices that comprise a single assay test path, and methods for their use. The single assay test path may contain one unique solid dried labeled detector reagent. In another embodiment the single assay test path contains more than one unique solid dried labeled detector reagents, e.g., two reagents, three reagents, or four reagents. For example, in one embodiment the present disclosure provides a lateral flow assay device for measuring an analyte having a solid support including absorbent material for providing capillary flow comprising: a) a test sample receiving region for receiving a test sample; b) a capture region comprising one or more solid dried labeled detector reagents in one or more localized sub-regions, e.g., spots, c) a test region comprising a capture reagent for the analyte; d) a reservoir region comprising absorbent material for providing capillary flow; wherein the sample region, capture region, test region, and reservoir region are in capillary flow communication, whereby the sample flows from the capture region, across the test region, and then into the reservoir region. The lateral flow assay device may have one assay test path, or two assay test paths, or three assay test paths, or four assay test paths, or more than four assay test paths, where each assay test path independently comprises one or more dried labeled detector reagents. The device does not require the presence of a barrier, e.g., a chemical or physical barrier, between assay test paths in order to keep the assay test paths distinct from one another, in other words, in a non-overlapping configuration.

In certain embodiments, the device includes more than two, for example, three, four, five, six or more, different assay test paths, with each assay test path containing the labeled detection reagents and capture reagents specific for different analytes of interest, such that the device can be used to detect the presence of three, four, five, six or more different analytes.

In a related aspect, kits for the simultaneous detection of multiple analytes, or components within a single liquid sample, are provided, such kits comprising a multiplex lateral flow assay device disclosed herein and, optionally, a container of a buffer, packaged together with instructions for using the device and buffer to detect the presence or absence of the analytes in a sample, such as a biological sample.

In a further aspect, methods for detecting the presence of a plurality of analytes of interest in a liquid test sample are provided. In certain embodiments, such methods comprise: (a) providing a multiplex lateral flow assay device described herein; (b) applying the test sample to the sample receiving region; (c) optionally applying a chase buffer to the sample receiving region; (d) allowing the test sample to contact a plurality of labeled detection reagents, each labeled detection reagent being specific for one of the plurality of analytes, whereby labeled detection reagent-analytes are formed if one or more of the analytes is present in the sample; and (f) allowing the labeled detection reagent-analytes to migrate through the capture membrane with each labeled detection reagent-analyte migrating along a specific assay test path to a test line that is specific for the specific analyte, wherein formation of a detectable signal at a specific test line is indicative of the presence of the specific analyte in the sample.

The above-mentioned and additional features of the present invention and the manner of obtaining them will become apparent, and the invention will be best understood by reference to the following more detailed description. All references disclosed herein are hereby incorporated by reference in their entirety as if each was incorporated individually This Brief Summary has been provided to introduce certain concepts in a simplified form that are further described in detail below in the Detailed Description. Except where otherwise expressly stated, this Brief Summary is not intended to identify key or essential features of the claimed subject matter, nor is it intended to limit the scope of the claimed subject matter.

The details of one or more embodiments are set forth in the description below. The features illustrated or described in connection with one exemplary embodiment may be combined with the features of other embodiments. Thus, any of the various embodiments described herein can be combined to provide further embodiments. Aspects of the embodiments can be modified, if necessary to employ concepts of the various patents, applications and publications as identified herein to provide yet further embodiments. Other features, objects and advantages will be apparent from the description, the drawings, and the claims.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION OF THE INVENTION

The present invention may be understood more readily by reference to the following detailed description of preferred embodiments of the invention and the Examples included herein.

The present invention provides devices and methods for detecting the presence of multiple analytes simultaneously in a sample, preferably a biological or environmental sample. As used herein, the term "analyte" encompasses proteins and/or peptides, including ligands and receptors; antibodies or antigen-binding fragments thereof; non-protein molecules, such as carbohydrates, phospholipids and nucleic acid molecules; small molecules; and other molecules of biological interest. Examples of biological samples that can be tested using the disclosed devices and methods include, but are not limited to, whole blood, serum, plasma, nasal secretions, sputum, urine, saliva, transdermal exudates, cerebrospinal fluid, and vaginal or urethral secretions. Fecal samples can also be tested following suitable processing. Examples of environmental samples that can be tested using the disclosed devices and methods include, but are not limited, to soils and food stuffs. Those of skill in the art will appreciate that solid and/or powdered materials can be tested following suspension in an appropriate buffer).

The term "test region" as used herein refers to a discrete location on a lateral flow test strip which is interrogated in order to generate a signal related to the presence or amount of an analyte of interest. Such interrogation may be performed visually as in an over-the-counter pregnancy test, or in an instrumented fashion as through the detection of reflectance, absorption, fluorescence, luminescence, etc. by a suitably configured meter.

The terms "proximal" and "distal" are not used in any functional sense, but rather simply to distinguish the two ends of the membrane or the test strip or the device of the present disclosure.

Figure 1:
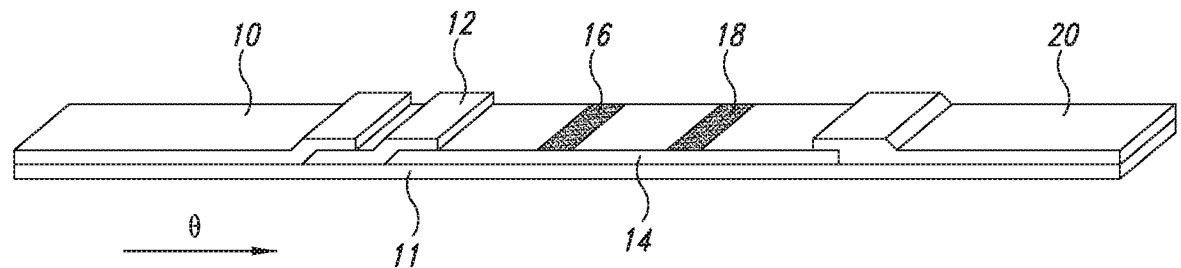
FIG. 1 shows a typical prior art lateral flow assay device.
Figures 2A, 2B:
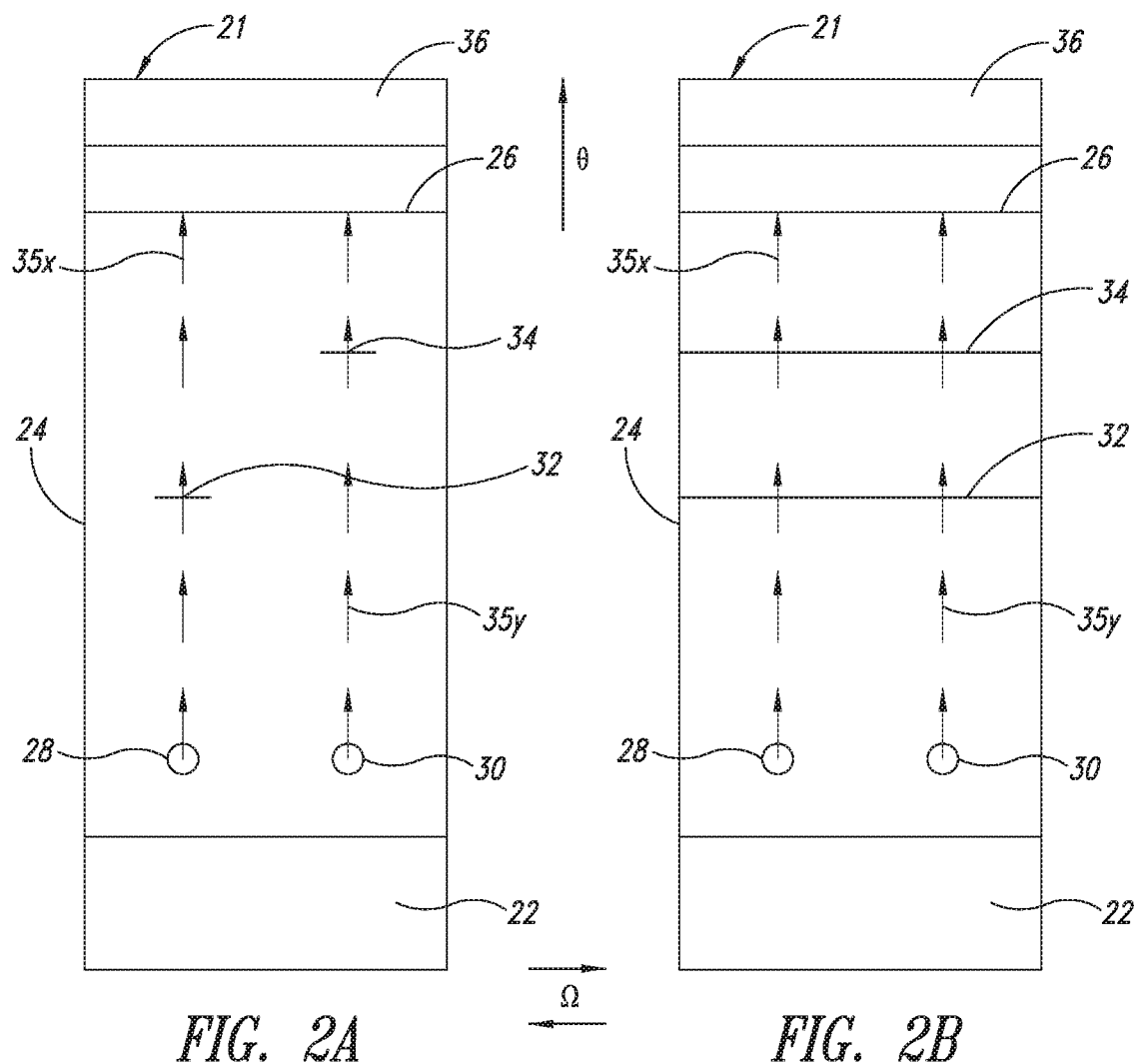
FIG. 2A shows a multiplex lateral flow assay device disclosed herein.
FIG. 2B shows a multiplex lateral flow assay device disclosed herein.

An embodiment of a lateral flow assay device 21 of the present disclosure for use in detecting two different analytes (analytes X and Y) is shown in FIG. 2A. Device 21 comprises a test sample receiving region which comprises a sample pad 22, which may also be referred to as a sample application pad 22. The sample pad 22 receives a liquid test sample suspected of containing at least one of the two different analytes. In one embodiment, sample pad 22 is used to buffer test samples for optimal reaction with immobilized detection reagents as detailed below, comprises a layer of support material that is capable of serving as a template for conjugate and sample application. In one embodiment, sample pad 22 may include at least one layer of material that aids in providing consistent liquid flow, wetting, buffering and pH maintenance of fluids, and/or aids in biological sample separation. In one embodiment, for serum and plasma based assays, a single layer of material that helps with consistent liquid flow, buffering, wetting and step wise mixing process can be used. In one embodiment, for assaying blood samples, sample pad 22 may include additional materials or treatments that can separate blood cells. Examples of appropriate materials are well known in the art.

Fluid flows in a theta ($\Theta$) direction from sample pad 22 laterally to, and downstream through, membrane 24 which is provided with two test lines 32 and 34, and a control line 26. The test lines 32 and 34 may extend partially across the device 21 as shown in FIG. 2A, or the test lines 32 and 34 may be in the form of stripes that extend continuously across the device 21 as shown in FIG. 2B. Membrane 24 is formed of materials generally employed in lateral flow test devices and well known to those of skill in the art, such as nitrocellulose, nylon which may optionally be charged-modified, and cellulose acetate. Nitrocellulose is a preferred membrane for the devices and methods of the present disclosure. Other suitable materials include polyvinylidene fluoride membrane, polyethersulfone membrane, porous polyethylene sheets, and glass fiber mats.

Following application of labeled detection reagents at regions 28 and 30, test lines 32 and 34, and control line 26, membrane 24 may be laminated with a series of synthetic and/or natural paper products of appropriate sizes and porosities.

A first labeled detection reagent, such as a labeled antibody, that is specific for analyte X is spotted and dried onto membrane 24 at region 28. Similarly, a second, different, labeled detection reagent that is specific for analyte Y is spotted and dried onto membrane 24 at region 30. A first capture reagent that is specific for analyte X is immobilized on membrane 24 at test line 32 and a second capture reagent that is specific for analyte Y is immobilized at test line 34. The immobilized capture reagents may be either spotted or striped completely across the membrane.

Control line 26, which is used as an internal control to ensure that all the test components are working, comprises molecules that bind to both of the detection reagents irrespective of the presence or absence of the analytes. For example, for antigen-antibody interactions, control line 26 may comprise anti-Protein A or human IgG immobilized on membrane 24.

An absorbent pad 36 is provided at, or in proximity to, the end of the flow path. Pad 36 absorbs any excess fluid and prevents any backflow of fluid towards sample pad 22. The absorbent pad 36 is located in the reservoir region of the device, which is positioned downstream of the capture membrane and provides a place for absorbing excess liquid, for example, excess liquid from either or both of the test sample and the chase buffer.

The liquid test sample contacts each of the two labeled detection reagents at regions 28 and 30 where the labeled detection reagents are mixed and, if either of analytes X and Y is present in the test sample, labeled detection reagent-analyte conjugates are formed. The labeled detection reagent-analyte conjugates and non-conjugated labeled detection reagents then flow longitudinally through the device, i.e., in the theta ($\Theta$) or downstream direction, with little to no perpendicular flow, i.e., little to no flow in an omega ($\Omega$) direction, such that individual and non-overlapping assay test paths 35$x$ and 35$y$ are formed for each of analytes X and Y, respectively. The first and second labeled detection reagents preferably have a low diffusion constant such that there is little to no lateral diffusion, i.e., diffusion in an omega ($\Omega$) direction as identified in FIG. 2A and FIG. 2B, of the first and second labeled detection reagents between the first and second assay test paths following solubilization by the liquid test sample. For clarity, and with reference to FIG. 2A, assay test path 35$x$ runs in a $\Theta$ direction from spot 28 to the control line 26, where the location of assay test path 35$x$ is illustrated by a series of arrow-terminated longitudinal lines collectively referred to as feature 35$x$. Likewise, assay test path 35$y$ runs in a $\Theta$ direction from spot 30 to the control line 26. As shown in FIG. 2A, a direct line drawn between region 28, which marks the beginning of a first assay test path 35$x$, and region 30, which marks the beginning of a second assay test path 35$y$, does not cross a barrier of any kind. In fact, in one embodiment, the entirety of assay test path 35$x$ and the entirety of assay test path 35$y$ are contained within a single, that is a shared, chamber, i.e., as viewed in the omega direction there is no barrier directly between the two test path. When there is no physical, chemical or other barrier between any two assay test paths, the test paths may optionally be sited on the same piece of capture membrane, i.e., the capture membrane is continuous in the omega direction between assay test paths such that there is no gap or break or cut in the membrane that is located directly between neighboring assay test paths. Once the flow reaches test lines 32 and 34, any labeled detection reagent-analyte conjugates bind to the capture reagents and become immobilized, resulting in detectable colored lines or rectangles at test lines 32 and 34. The non-conjugated labeled detection reagents continue to travel along the individual assay test paths and bind to, and are immobilized at, control line 26 resulting in a detectable colored line. If a colored line is not observed at control line 26, the test is considered invalid. Excess liquid is then taken up in the reservoir region which holds an absorbent pad 36.

Multiple spots of labeled detection reagents may be present in any given assay test path, thereby having a multiplicative effect on the number of analytes that can be detected in a single test sample. As a result, the present disclosure provides a very dense, easy to produce, multiplexed assay within a very small device footprint. In one embodiment, the size of the test strip of the present disclosure is about 40-80 mm in length about 10-30 mm in width, while in another embodiment the test strip is about 50-70 mm in length and about 15-25 mm in width. In one embodiment, the capture membrane is about 10-40 mm in length, while in another embodiment the capture membrane is about 20-30 mm in length.

The spots of labeled detection reagents are present in localized geographical regions of the capture region of the capture membrane, or in other words, localized geographical regions refer to spots. The size of each spot is about 1-50 $mm^2$. In various embodiments, a spot occupies an area of about 1 $mm^2$, or 2 $mm^2$, or 3 $mm^2$, or 4 $mm^2$, or 5 $mm^2$, or 6 $mm^2$, or 7 $mm^2$, or 8 $mm^2$, or 9 $mm^2$, or 10 $mm^2$, or 11 $mm^2$, or 12 $mm^2$, or 13 $mm^2$, or 14 $mm^2$, or 15 $mm^2$, or 16 $mm^2$, or 17 $mm^2$, or 18 $mm^2$, or 19 $mm^2$, or 20 $mm^2$, or 30 $mm^2$, or 40 $mm^2$, or 50 $mm^2$, where the size of the spot may be described by a range selected from any two of the stated values, e.g., a range of 10-15 $mm^2$. The spot may have a symmetrical shape, e.g., a circular, square or rectangular shape. When the spot has the form of a circle, the circle may have a diameter of about 0.5-5 $mm^2$, or about 1-3 $mm^2$. In one embodiment, the spots present in the capture region do not overlap with one another.

The spots may be placed at a distance from one another, where that distance is measured by the distance between a mid-point of each spot, where those two spots are the most closely located spots, and the distance is about 1-10 mm. In various embodiments, the spots are located a distance from one another of at least 1 mm, or 2 mm, or 3 mm, or 4 mm, or 5 mm, or 6 mm, or 7 mm, or 8 mm, or 9 mm, or 10 mm, and not more than about 30 mm, or 25 mm, or 20 mm, or 15 mm, or 10 mm, or 9 mm, or 8 mm, or 7 mm, or 6 mm, or 5 mm, or 4 mm, or 3 mm, where the distance between closest spots may also be described as being within a range between two values selected from the stated values, e.g., a distance of 1-5 mm.

Thus, in one embodiment the test strip of the present disclosure has four assay paths, each assay path beginning with a spot comprising dry labeled detection reagent and optionally being in the shape of a circle having a diameter of about 1.5-2.5 mm, where two closest spots are about 2.5-3.5 mm from one another measured from the center of each of the two closest spots.

In another embodiment the test strip of the present disclosure has three assay paths, each assay path beginning with a spot comprising dry labeled detection reagent and optionally being in the shape of a circle having a diameter of about 1.5-2.5 mm, where two closest spots are about 2.5-3.5 mm from one another measured from the center of each of the two closest spots.

In another embodiment the test strip of the present disclosure has two assay paths, each assay path beginning with a spot comprising dry labeled detection reagent and optionally being in the shape of a circle having a diameter of about 1.5-2.5 mm, where two closest spots are about 2.5-3.5 mm from one another measured from the center of each of the two closest spots.

In another embodiment the test strip of the present disclosure has one assay path, the assay path beginning with a spot comprising dry labeled detection reagent and optionally being in the shape of a circle having a diameter of about 1.5-2.5 mm.

When a second spot is located on a single assay test path, that second spot may be about 2.5-3.5 mm distant from the first spot, and of essentially the same size as the first spot.

Figure 3A:
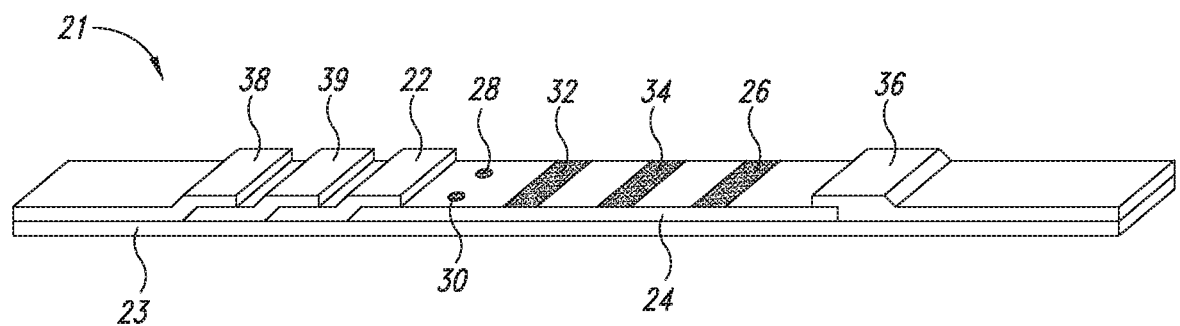
FIG. 3A shows a perspective view of a multiplex lateral flow assay device of the present disclosure.

FIG. 3A shows a test strip 21 of the present invention. The test strip 21 and components thereof have a proximal end and a distal end, where the flow direction Θ of a test sample is from the proximal end to the distal end of the test strip or component thereof. When the observer looks down onto the test strip 21, the test strip 21 and components thereof have a left edge and a right edge, where the proximal end is closest to the observer and the distal end is furthest from the observer.

The test strip 21 comprises a sample application pad 22 which is upstream from and in direct contact with a porous membrane 24. The pad 22 may be prepared from materials known in the art for this purpose, e.g., woven meshes and cellulose filters. Suitable materials for an application pad are available from Ahlstrom Corporation (Helsinki, Finland), for example, their CytoSep® media may be used to form an application pad 22. CytoSep® media has the property that it is a single layer media consisting of high purity natural and synthetic fibers, where the untreated media contains no chemical interfering substances and shows to significant binding of plasma components. CytoSep® media retains red blood cells while allowing serum to flow rapidly. In one embodiment the application pad is a cellulose filter.

The test strip 21 optionally comprises a backing card 23, which may also be referred to as a support card or support film. The backing card is preferably impermeable to water. The sample application pad 22 and other features of the test strip 21 may be adhered to the backing card 23. The backing card 23 is rigid or semi-rigid so that the test strip maintains a flat shape. The backing card may be formed from materials known in the art for this purpose, e.g., mylar.

The test strip 21 comprises a porous membrane 24. The membrane 24 allows a flow of aqueous test sample and, when used, chase buffer, from a proximal end of the membrane, i.e., the end of the membrane in contact with the sample application pad, to the furthest opposite end of the membrane, i.e., the distal end of the membrane.

The membrane 24 of test strip 21 comprises control line 26. Control line 26, which is used as an internal control to ensure that all the test components are working, comprises molecules that bind to both of the detection reagents irrespective of the presence or absence of the analytes. For example, for antigen-antibody interactions, control line 26 may comprise anti-Protein A or human IgG immobilized on membrane 24.

The membrane 24 of test strip 21 comprises one or more spots at the proximal end of the membrane which contain solid labeled detection reagents that is or are specific for analyte(s) of interest. In FIG. 3A, two spots 28 and 30 are shown. The spots 28 and 30 are located directly on and therefore are in contact with the membrane 24.

The membrane 24 of test strip 21 comprises one or more test lines located between the control line 26 and the spots 28 and 30. Each test line contains an immobilized capture reagent that is specific for an analyte of interest. In FIG. 3A, two test lines 32 and 34 are shown.

The test strip 21 comprises an absorbent pad 36. The absorbent pad 36 is located at the distal end of the test strip shown in FIG. 3A. The primary function of the absorbent pad is to absorb the water and solubilized components present in the test sample and the chase buffer after they pass through the test lines and the control line. As the desired volume of test sample and/or chase buffer is increased, the holding capacity of the absorbent pad should likewise be increased. A suitable absorbent pad 36 may be prepared from, e.g., cellulose filters. The flow of liquid into the absorbent pad may not be laminar, which leads to uneven flow of the solvent front down the membrane. To address the consequences of a non-laminar flow, in one embodiment the test strips of the invention include an intermediate absorbent pad (not shown in FIG. 3A) which is located between the absorbent pad 36 and the distal end of the membrane 24. The intermediate absorbent pad may be more porous than the absorbent pad, thereby allowing entering solvent to evenly distribute in a direction perpendicular to the flow of the solvent. After passing through the intermediate absorbent pad, the solvent and dissolved components more evenly enter the absorbent pad, i.e., enter the absorbent pad 36 with an enhanced laminar flow.

In use, the sample application pad 22 can receive both the test sample and thereafter receive the chase buffer. However, in one embodiment of the test strip of the invention, a separate buffer pad 38 is provided to receive the chase buffer. The buffer pad 38 is located upstream of the application pad 22, at the proximal end of the test strip 21. The buffer pad may be made from the same materials that are used to prepare the application pad. However, by having the application pad 22 separate from the buffer pad 38 it is possible to select different materials for the two different pads, and/or differentially treat the application pad 22 and the buffer pad 38 so that they have different properties.

The buffer pad 38 may optionally be located directly next to the application pad 22 (not shown in FIG. 3A) or alternatively a hydrophobic pad 39 may be positioned between the application pad 22 and the buffer pad 38 as shown in FIG. 3A. In one embodiment the hydrophobic pad 39 has a different hydrophobicity compared to the hydrophobicity of the application pad 22. In one embodiment the hydrophobic pad 39 has a different hydrophobicity compared to the hydrophobicity of the buffer pad 38. In one embodiment, the hydrophobic pad 39 is more hydrophobic compared to the hydrophobicity of each of the buffer pad 38 and the application pad 22, i.e., the buffer pad 38 and the application pad 22 are each less hydrophobic than the hydrophobic pad 39. The relative hydrophobicity of two adjacent pads is readily determined by placing an aqueous sample onto one or both of the adjacent pads: the aqueous sample will tend to migrate to the more hydrophilic pad, i.e., the less hydrophobic pad, all other factors being equal.

Figure 3B:
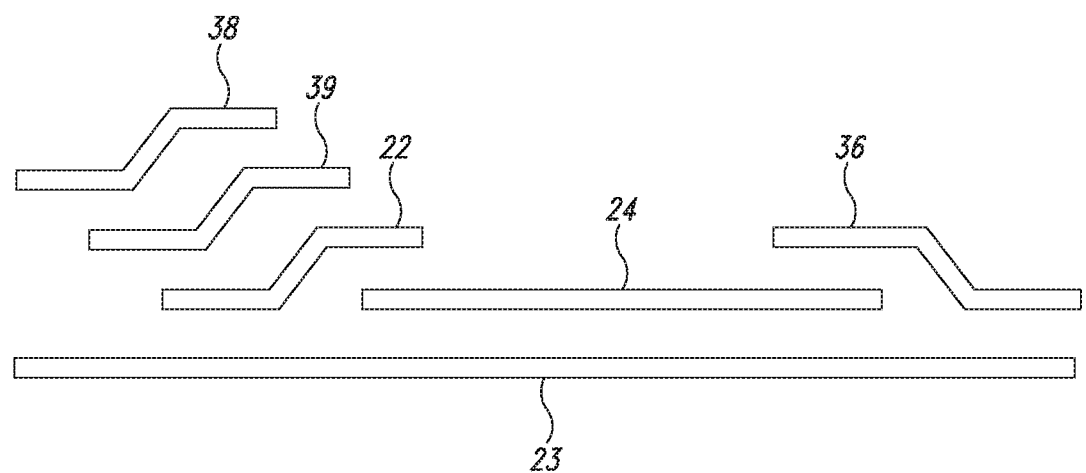
FIG. 3B shows an exploded side view of the multiplex lateral flow assay device of FIG. 3A.

FIG. 3B shows an exploded side-view of the test strip 21 of FIG. 3A. In FIG. 3A, 22 is the sample application pad, 23 is the backing card, 24 is the capture membrane, 36 is the absorption pad, 38 is the buffer pad and 39 is the hydrophobic pad.

Figure 3C:
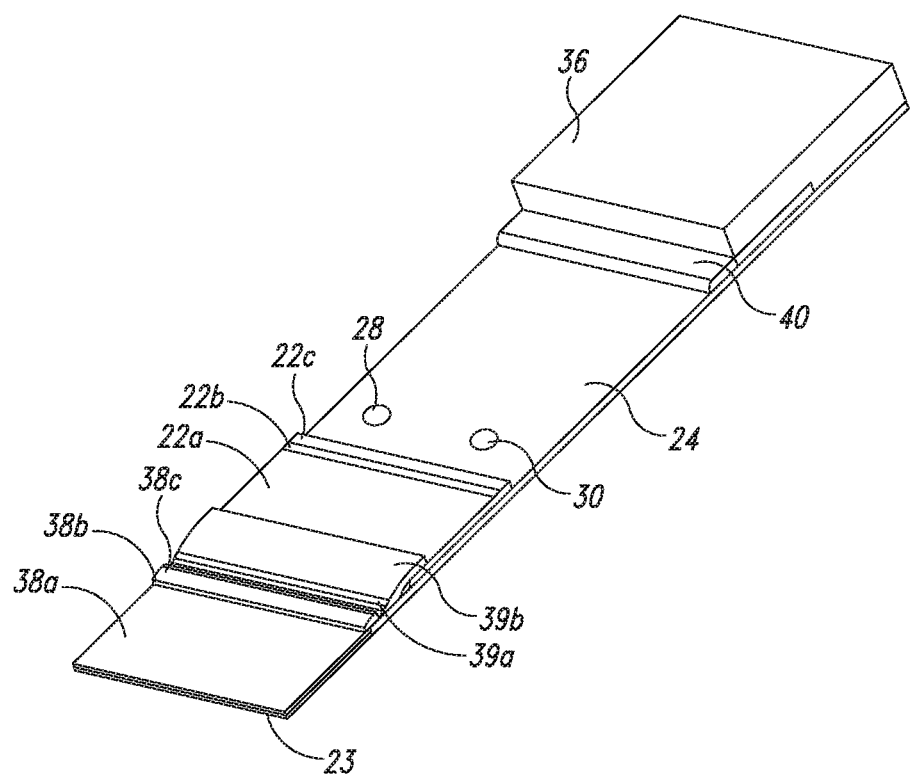
FIG. 3C shows a perspective view of a multiplex lateral flow assay device of the present disclosure.

FIG. 3C shows a view of an embodiment of a test strip of the present invention. The test strip comprises a membrane 24. At the distal end of the test strip is located an absorption pad 36. Positioned between the membrane 24 and the absorption pad 36 is an intermediate absorption pad 40. In one embodiment, the intermediate pad 40 is more porous than the pad 36. In one embodiment, the intermediate pad 40 is more hydrophilic than the pad 36. The hydrophilicity of the intermediate pad may be increased by adding detergent or surfactant to the intermediate pad. The pad 36 has a larger volume than the pad 40 and so liquid will preferentially wick into and remain in the pad 36. The presence of the intermediate pad 40 may enhance the laminar flow of the liquid as it travels down the test strip, thus providing a more defined readout.

At the proximal end of the test strip is located a buffer pad 38 which may be seen to have three regions, 38a, 38b and 38c. Region 38a is laminated to the backing card 23. Region 38c sits on top of hydrophobic pad 39. By sitting on top of the hydrophobic pad 39, the buffer pad 38 is more readily able to transfer chase buffer in a downstream direction. Region 38b transitions between regions 38a and 38c. Adjacent to the buffer pad 38, in a downstream direction, is the hydrophobic pad 39 which is seen to have two regions, 39a and 39b. Region 39b sits on top of application pad 22. By sitting on top of the application pad 22, there is greater contact between the hydrophobic pad 39 and the application pad 22, and therefore the hydrophobic pad 39 is more readily able to transfer chase buffer in a downstream direction. Region 39a of the hydrophobic pad transitions between a region (not shown) of the hydrophobic pad which is laminated to the backing card 23, and the region 39b which sits on top of the application pad 22. Adjacent to the hydrophobic pad 39, in a downstream direction, is the application pad 22 which may be seen to have three regions, 22a, 22b and 22c. Region 22a is laminated to the backing card 23. Region 22c sits on top of the membrane 24. By sitting on top of the membrane 24, there is more contact between the application pad 22 and the membrane 24, and therefore the application pad 22 is more readily able to transfer sample to the membrane 24. Region 22b of the application pad transitions between regions 22a and 22c. The pads and regions in the devices of the present may be said to be in operable fluid communication with one another since liquid is able to flow from one location to another location on the device.

Figure 3D:
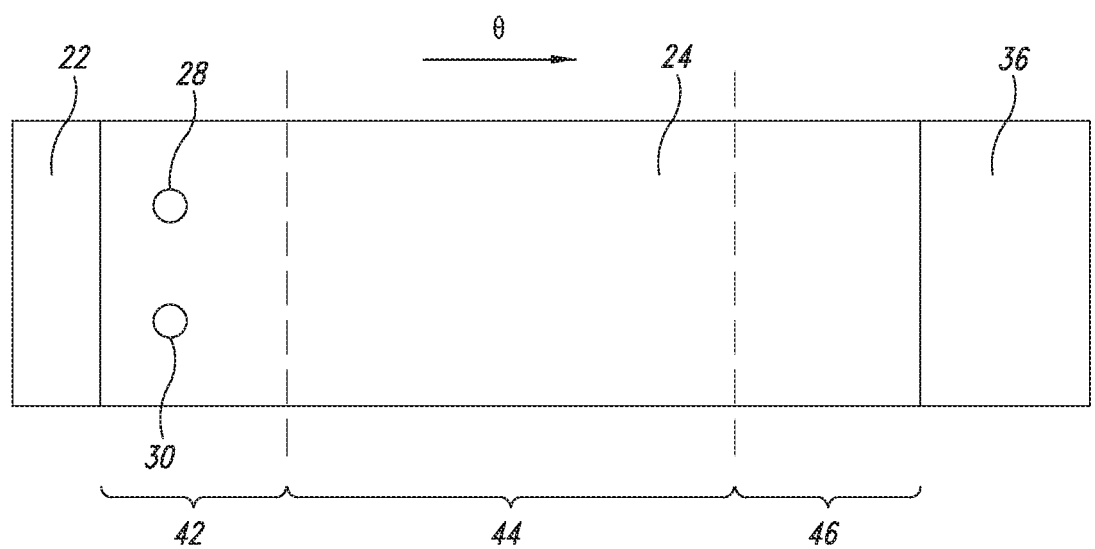
FIG. 3D shows a capture membrane of the present disclosure with flanking test sample receiving region and reservoir region according to the present disclosure.

FIG. 3D illustrates an embodiment of the invention comprising two spots of solid labeled detection reagents, specifically spots 28 and 30, which are located on the capture membrane 24. The capture membrane 24 is flanked on opposing sides by the sample application pad 22 at the proximal end of the capture membrane 24 and by the absorption pad 36 at the distal end of the capture membrane 24. FIG. 3D shows how the capture membrane 24 may be divided into functional regions, namely region 42 which is referred to as the capture region, region 44 which is referred to as the test region, and region 46 which is referred to as the control region. Thus, FIG. 3D shows a test sample application pad 22, a capture membrane 24, and an absorption pad 36, the application pad located directly adjacent to a proximal end of the capture membrane 24, the absorption pad located at a distal end of the capture membrane 24, where a test sample flows in a downstream direction Θ from the test sample application pad to the absorption pad, where the capture membrane comprises i) a capture region directly adjacent to the application pad, ii) a test region directly adjacent to the capture region and not adjacent to the application pad, and ii) a control region directly adjacent to the test region and not adjacent either to the test region or the capture region.

While FIG. 3D shows a capture membrane with two spots 28 and 30, each spot comprising a unique solid labeled detection reagents, the invention provides that any of 1, 2, 3, 4, 5, 6, 7, 8, 9, 10, or more spots comprising solid labeled detection reagents may be present in the capture region. In various embodiments, the capture membrane of a test strip of the invention has 1-8 spots, or 2-6 spots, or at least 2 spots, or at least 3 spots, or at least 4 spots, or at least 5 spots, or at least 6 spots, or at least 7 spots, or 8 spots. Those spots will be distinct from one another, in other words, two spots do not overlap.

After the test sample enters the capture region, it will contact the various spots and then continue onwards in the Θ direction. Contact between a spot and the test sample initiates an assay test path, at least so long as the assay test path has not already been initiated by a different spot. In other words, if an assay test path is initiated at a first spot, the fact that the assay test path passes through a second spot does not cause the initiation of a second assay test path: the second spot is located within the assay test path initiated by the first spot. An assay test path starts at a spot and then extends from that spot in a downstream direction, the test path running in a substantially straight line towards the distal end of the capture membrane. Thus, if a second spot is located within an assay test path initiated by a first spot, the second spot does not initiate a new assay test path. Each assay test path runs in a longitudinal direction, i.e., in the direction Θ after being initiated at a spot. Preferably, no two assay test paths overlap with one another, i.e., a test path has little or no movement in an Ω direction which is perpendicular to the flow of the sample.

Figure 3E:
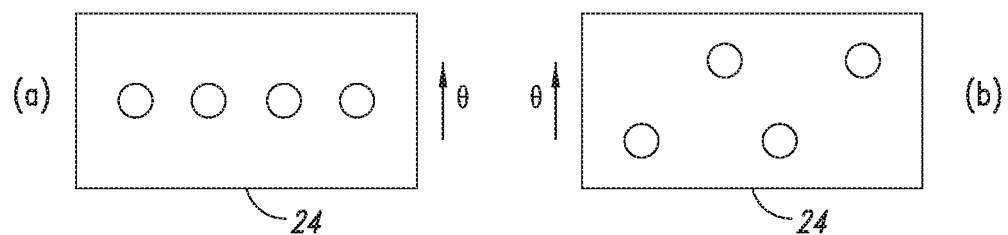
FIG. 3E in panels (a), (b), (c) and (d) shows four options for placing spots in the capture region of a capture membrane according to the present disclosure.
Figure 3E:
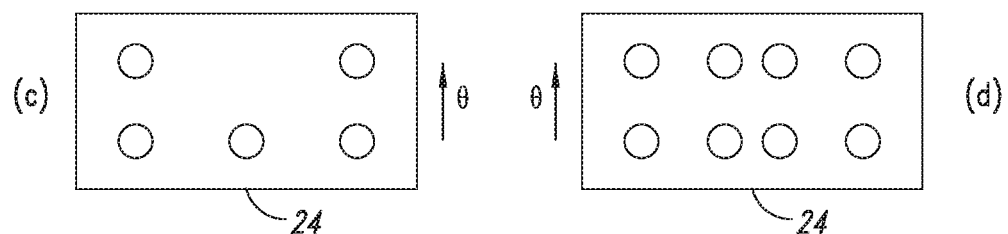

The spots may be placed at any locations within the capture region, so long as they do not overlap with one another. For example, as illustrated in FIG. 3E, the capture region may have 4 spots in a straight line (a); 4 spots in a staggered arrangement (b); 5 spots in an "M" arrangement (c); or 8 spots placed in two parallel lines (d), where these are four examples selected from a large number of possibilities. The arrangement of spots in (a) gives rise to four assay test paths; the arrangement of spots in (b) gives rise to four assay test paths, the arrangement of spots in (c) gives rise to three assay test paths, and the arrangement of spots in (d) gives rise to four assay test paths. In FIG. 3E the spots are shown as having a circular shape, and indeed that is one optional shape for the spots. However, the spots may adopt other shapes, e.g., square, rectangle, oval, triangular, etc.

In the various embodiments of the invention disclosed herein, each spot may contain a unique solid labeled detection reagent which will react with a unique analyte of interest that is potentially present in the test sample. However, in an optional embodiment the same solid labeled detection reagent may be present in two or more different spots, where this embodiment may be useful to confirm the result observed from having the solid labeled detection reagent in only a single spot, i.e., to provide a duplicative result in order to enhance the observer's confidence in the test results. In another optional embodiment, a single spot may contain more than one unique solid labeled detection reagent, i.e., a single spot may contain multiple unique detection reagents which are specific for multiple unique analytes, e.g., a spot may contain two different solid labeled detection reagents, one of which reacts with analyte X and the other of which reacts with analyte Y. Thus, each spot in the capture region may contain 1, 2, or more unique labeled detection reagents, each of which is specific for a different analyte, and furthermore, any two spots may contain the same labeled detection reagent. In one embodiment each spot contains a different labeled detection reagent. In one embodiment none of the spots contains more than one labeled detection reagent, so that each spot contains reagent that is specific for only one analyte.

After being initiated at a spot in the capture region, the assay test path extends through the test region. Each assay test path will extend across one or more test lines located in the test region. Each of the one or more test lines that are present in the test region 44 of a capture membrane 24 of the invention may be striped continuously across the membrane or may be localized at one or more locations across the membrane. In reference to test lines in the test region, across refers to the Ω direction, which is perpendicular to the flow of the sample, referred to as the Θ direction. As a few examples of test line configurations are:
  a. each of two test lines i and ii may extend fully and continuously across the membrane (a); or
  b. test line i may extend partially across the membrane in a number of distinct locations such as three distinct locations while test line ii extends fully and continuously across the membrane (b); or
  c. test line i may be continuous across a portion of the membrane and then localized at two locations, while test line ii is localized at four locations (c); or
  d. test line i may extend continuously but not completely across the membrane, and test line ii may be localized at a single location along the test line (d).

Figure 3F:
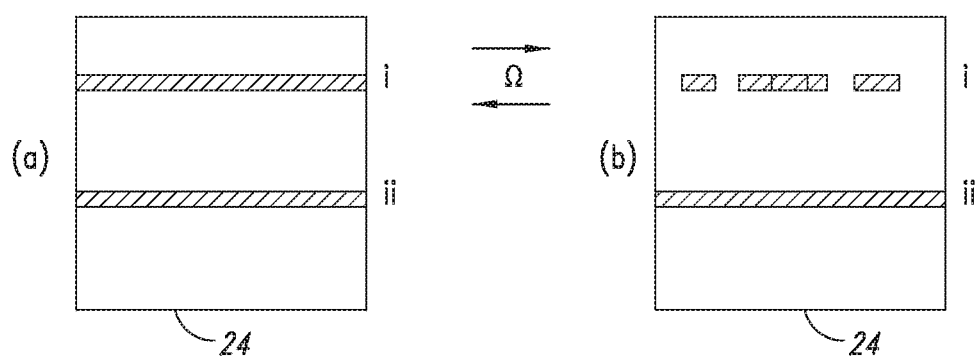
FIG. 3F in panels (a), (b), (c) and (d) shows several options for constructing test lines in a test region of a capture membrane according to the present disclosure.
Figure 3F:
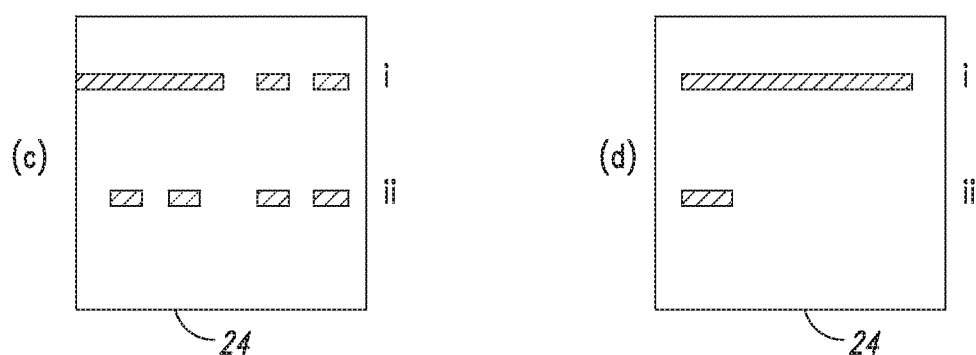

While FIG. 3F shows four test regions each having two test lines, a test region of any of the embodiments of the present disclosure may have exactly 1, or exactly 2, or exactly 3, or exactly 4, or exactly 5, or exactly 6, or exactly 7, or exactly 8, or exactly 9, or exactly 10, or more than 10 test lines. Also, while FIG. 3F shows four pairs of test line configurations, each test line in a test region may have a configuration that is independent from the configuration of another test line in the same test region.

Detection reagents that can be effectively employed in the disclosed devices are well known to those of skill in the art and include antigens, antibodies, nucleic acid molecules, and other relevant protein or non-protein molecules. For example, the detection reagent can comprise an antibody that specifically binds to a known disease antigen. Each of the detection reagents is labeled with a reporter agent.

Examples of reporter agents that can be used in the devices, kits and methods disclosed herein include, but are not limited to, colloidal nanoparticles (such as gold nanoparticles), latex microspheres, quantum dots, enzymes, fluorophores and the like. Descriptions of gold nanoparticles can be found in, e.g., Colloidal Gold: Principles, Methods, and Applications, Vol. 1, Editor M. A. Hayat, Academic Press (1989) and "Nanoparticles in Biology and Medicine, Methods and Protocols" Editor Mikhail Soloviev, Springer Protocols, Methods in Molecular Biology, vol. 906 (2012), e.g., Chapter 4. A description of fluorescent europium(III) nanoparticles and colloidal gold reporters can be found in, e.g., Juntunen, E., et al., Analytical Biochemistry, 428(1): 31-38 (2012). A description of iron nanoparticles can be found in, e.g., Liu, C. et al., Anal. Chem., 83(17):6778-6784 (2011). A description of reporter agents detectable by near-infrared spectroscopy is described in, e.g., Swanson, C. and D'Andrea, A., Clinical Chemistry, 59(4):641-648 (2013). A description of reporter agents detectable by fluorescence is described in, e.g., Xu, Y. et al., Anal. Chem., 86(12):5611-5614 (2014). Descriptions of quantum dots are described in, e.g., Fabio Cimaglia, F., et al., Nanotechnology Development, 2(1):26-30 (2012). In certain embodiments, the reporter agent has a particle diameter greater than or equal to 8 nm, such as 20 nm or 40 nm. In certain embodiments, particles labeled with enzymes that may provide enhanced signals upon the addition of a substrate in this same multiplexed format are included.

The reporter agent and/or labeled detection reagent preferably has a sufficiently low diffusion constant (with an effective membrane diffusion constant of typically $D_{\mathit{eff}} < 10^{-8}$ m$^2$/sec) whereby when a liquid sample containing the analyte of interest contacts the labeled detection reagent, the resulting labeled detection reagent-analyte conjugate is carried in a generally longitudinal, unidirectional, nearly uniform flow based on capillary action towards the test and control lines but with little to no perpendicular flow (in the Ω direction) towards the lateral edges of membrane 24.

To place the labeled detection reagents in the capture region of a capture membrane according to the present disclosure, the labeled detection reagents may be prepared in solution form, and then an aliquot of that solution deposited onto the capture membrane to effective create a spot on the capture membrane, where that spot comprises the labeled detection reagent. Initially the spot will include solvent, which is typically water and may optionally include other solvents. Thus, the spot will initially be wet. However, the solvent will evaporate from the spots located on the capture membrane thereby leaving behind spots comprising dried labeled detection reagents. In one embodiment, the present invention provides spots comprising labeled detection reagents that are in solvent-free form. The solutions used to create the spots may be referred to herein as spotting solutions.

In one embodiment, the spotting solution are aqueous solutions, i.e., on a weight basis they contain mostly water. In addition, the spotting solutions contain labeled detection reagents. Such reagents are designed to react with an analyte of interest present in a test sample, and to have a reporter group that can be visualized in order to allow determination of whether the labeled detection reagent did or did not react with an analyte of interest. Labeled detection reagents are well known in the art, and the manufacture and use of aqueous compositions comprising labeled detection reagents is well known in the art. Labeled detection reagents are sometimes referred to by terms, such as detector reagents, labeled biorecognition molecules, recognition element and labelled analyte, by those skilled in the art. However, the prior art typically places a labeled detection reagent in or on the conjugate pad component of a device used in a lateral flow assay, prior to initiating the assay by adding the test sample, while the present invention provides devices and methods wherein the labeled detection reagent is placed directly on the capture membrane, e.g., a nitrocellulose membrane, prior to initiating the assay, and in one embodiment entirely omits the presence and use of a conjugate pad.

In addition to water and labeled detection reagent, a spotting solution of the present disclosure may include one or more water-soluble, non-volatile organic molecules (WNO). A WNO is soluble in water, and when measured at 20° C., has a solubility of at least 1 g/100 g of water, or at least 5 g/100 g of water, or at least 10 g/100 g of water, or at least 20 g/100 g water, or at least 30 g/100 g water, or at least 40 g/100 g water, or at least 50 g/100 g water. In one embodiment the WNO is a polyhydric compound, i.e., it contains a plurality of hydroxyl groups. The plurality may be selected from two, three, four, five, six, seven, eight, nine, ten, eleven, twelve, or more than twelve hydroxyl groups. In one embodiment, the WNO comprises a monosaccharide or a polysaccharide such as a disaccharide. Exemplary saccharide WNOs include the monosaccharides fructose, glucose and galactose, the disaccharides sucrose, lactose, maltose, trehalose, and the polysaccharides starch, dextrin, cellulose, pectin and glycogen. In various embodiments of the invention, the spotting solution contains at least 1 wt % WNO, or at least 2.5 wt % WNO, or at least 5 wt % WNO, or at least 7.5 wt % WNO, or at least 10 wt % WNO, or at least 15 wt %, including ranges selected from these values, e.g., between 10 and 15 wt %. In one embodiment the spotting solution comprises a disaccharide, and optionally comprises a mixture of two or more disaccharides, e.g., 5% sucrose and 5% trehalose, or other combinations of disaccharides.

In one embodiment the WNO comprises polyvinylalcohol (PVA) which may optionally include vinyl acetate units, i.e., some of the hydroxyl groups in the PVA may be acetylated. The water solubility of PVA depends in large part on its degree of hydrolysis (more highly acetylated PVA tends to have lower water solubility), and on its molecular weight (lower molecular weight tends to be more water soluble). The spotting solutions of the present invention may contain PVA, where the PVA may be present at a concentration of, e.g., 0.1 wt %, or 0.25 wt %, or 0.5 wt %, or 0.75 wt %, or 1.0 wt %, or 1.25 wt %, or 1.5 wt %, or 1.75 wt %, or 2 wt %, including ranges selected from these values, e.g., 0.75-1.25 wt % and 0.5-1.5 wt %.

In one embodiment, the spotting solution contains 7.5-12.5 wt % disaccharide and 0.5-2.0 wt % PVA, e.g., about 10 wt % disaccharide and about 1 wt % PVA. The disaccharide may be two different disaccharides, e.g., sucrose and trehalose, and the two different disaccharides may be present at a weight ratio of 1:10 to 10:1, e.g., 1:1. Increasing the PVA content above about 5 wt % causes a delay in release of the labelled detection reagent from the membrane, which may enhance the visibility of the signal but this also increases the assay time. A PVA concentration of about 0.5-1.5 wt % provides a good balance of properties.

Thus, in one embodiment, the dried spots of the present invention, when they are present on the capture membrane prior to initiating the assay, comprise saccharide, e.g., disaccharide. Optionally they contain two disaccharides, e.g., sucrose and trehalose. In one embodiment, the dried spots of the present invention, when they are present on the capture membrane prior to initiating the assay, comprise PVA. Optionally, the dried spots of the present invention, when they are present on the capture membrane prior to initiating the assay, comprise saccharide, e.g., disaccharide such as a mixture of sucrose and trehalose, and in addition comprise polyvinylalcohol (PVA).

In one embodiment the spotting solution contains surfactant, also known as detergent. The surfactant may be a water-soluble non-volatile organic molecule (WNO) where exemplary WNO surfactants are polyhydric nonionic surfactants such as polysorbate-type nonionic surfactants, e.g., Tween-20™, which is also known as 2-[2-[3,4-bis(2-hydroxyethoxy)oxolan-2-yl]-2-(2-hydroxyethoxy)ethoxy] ethyl dodecanoate and polysorbate 20. Other polysorbate surfactants are polysorbate 60 and polysorbate 80. The surfactant constitutes a small amount of the spotting solution, e.g., 0.01% (in a vol/vol basis for a liquid surfactant), or 0.02%, or 0.03%, or 0.04%, or 0.05%. Increasing the concentration of surfactant in the spotting solution causes the resulting spots to more quickly release the labeled detection reagent when that reagent contacts an analyte of interest. Too much surfactant in the spotting solution causes the resulting signals in the test region to become diffuse and perhaps overlap. A surfactant concentration of about 0.01-0.10%, or about 0.01-0.05% provides a good balance of performance properties.

The spots may be prepared by depositing a desired volume of spotting solution onto the capture membrane and then letting the solvent, principally water, evaporate so that the spots feel dry to the touch. The amount of spotting solution that is deposited on the membrane can vary, depending in part on the sensitivity of label component of the labeled detection reagent. Exemplary volumes of spotting solution used to create the spots of the invention include 0.1 µL, 0.2 µL, 0.3 µL, 0.4 µL, 0.5 µL, 0.6 µL, 0.7 µL, 0.8 µL, 0.9 µL and 1.0 µL, including ranges defined any two of these values, for example, 0.3-0.7 µL.

In one embodiment, the present disclosure provides a lateral flow assay device such as a lateral flow test strip, wherein the spotting solution, and therefore the region(s), e.g., the dry (effectively water free) spot or stripe that is created on the capture membrane of the assay device, comprises labeled detection reagent (which comprises a reporter group such as gold) in combination with a surfactant. In one embodiment, the present disclosure provides a lateral flow assay device such as a lateral flow test strip, wherein the spotting solution, and therefore the region(s), e.g., the dry (effectively water free) spot or stripe that is created on the capture membrane of the assay device, comprises labeled detection reagent (which comprises a reporter group such as gold) in combination with water soluble non-volatile organic compound (WNO). The WNO is non-volatile so that it does not evaporate from the spotted region after it has been applied to the spotted region, and is water soluble so that it is solubilized by the aqueous sample when that samples travels from the sample pad to the dry location of the labeled detection reagent. Examples of WNO compounds include polyhydric organic compounds and polyethers such as poly(ethylene glycol) and derivatives thereof, collectively known as PEGs and water-soluble derivatives thereof. In embodiments, the WNO is a polyhydric organic compound, an example of which is a saccharide, e.g., monosaccharides, disaccharides, trisaccharides, etc. and derivatives and analogs thereof which are water soluble, and another example is a poly(vinyl alcohol), also known as a PVA. In one embodiment, the present disclosure provides a lateral flow assay device such as a lateral flow test strip, wherein the spotting solution, and therefore the region(s), e.g., the dry (effectively water free) spot or stripe that is created on the capture membrane of the assay device, comprises labeled detection reagent (which comprises a reporter group such as gold) in combination with both of a surfactant and a WNO. In one embodiment, the spotting solution, and the spots that are on the capture membrane, comprise labeled detection reagent, disaccharide, surfactant, and polyvinylalcohol (PVA). An exemplary spot comprises PVA, Tween-20™, sucrose and trehalose in addition to labeled detection reagent. In one embodiment, on a weight basis, the spots contain more disaccharide than PVA, and contain more PVA than surfactant.

The embodiment of an assay device of the present disclosure which may be used to receive a test sample and then detect the presence of an analyte as described herein, and which has a region comprising anhydrous labeled detection reagent in combination with one or both of a surfactant and a WNO located directly on the capture membrane, may have a single assay test path, or it may have multiple assay test paths. Independently, an assay test path may have a single labeled detection reagent, or it may have multiple labeled detection reagents. In one embodiment, the device has a single assay test path comprising a single labeled detection reagent. In one embodiment, the device has a single assay test path comprising two, three, four, or more labeled detection reagents. In one embodiment, the device has two, three, four or more assay test paths, where each of the assay test paths comprises a single labeled detection regent. In one embodiment, the device has two, three, four or more assay test paths, where each of the assay test paths comprises multiple, e.g., two, three, four, etc. labeled detection regents.

In exemplary embodiments, the present disclosure thus provides:

1) A lateral flow assay device for detection of a presence of at least a first analyte of interest in a single liquid test sample, the device comprising:
   a. a test sample receiving region; and
   b. a capture membrane comprising a capture region, the capture region comprising a dry composition comprising an immobilized labeled detection reagent specific for the first analyte of interest, and at least one of a surfactant and a water soluble non-volatile organic compound in combination with the labeled detection reagent.
2) The device of embodiment 1, wherein the labeled detection reagent has a low diffusion constant such that there is little to no lateral diffusion of the labeled detection reagent following solubilization by the liquid test sample.
3) The device of embodiment 1, wherein the labeled detection reagent is in dry form on the capture membrane and the capture membrane is formed from nitrocellulose.
4) The device of embodiment 1, wherein the labeled detection reagent comprises a reporter agent selected from the group consisting of: colloidal nanoparticles, latex microspheres, quantum dots, enzymes and fluorophores.
5) The device of embodiment 4, wherein the reporter agent comprises gold nanoparticle.
6) The device of embodiment 1, wherein the immobilized labeled detection reagent is in combination with a water-soluble non-volatile organic molecule selected from the group consisting of disaccharide and polyvinylalcohol (PVA).
7) The device of embodiment 1, wherein the immobilized labeled detection reagent is in combination with a surfactant.
8) The device of embodiment 1, further comprising a test line that extends continuously across the capture membrane and intersects with the assay path of the capture membrane.
9) The device of embodiment 1, further comprising a control line positioned downstream of the test line, the control line comprising an immobilized control reagent that binds to the labeled detection reagent.
10) The device of embodiment 1, further comprising a reservoir region positioned downstream of the capture membrane for absorbing an excess of liquid.

In use, the liquid test sample is applied onto sample pad 22, followed by an optional buffer which may be referred to as the chase buffer. The chase buffer employed may be adjusted depending on the analyte to be detected. A typical chase buffer contains a salt, detergent, protein solution and preservative, and has a pH in the range of 6 and 10, for example between 7 and 8. In some cases, other or fewer components are employed in the chase buffer as required to achieve the desired specificity and sensitivity. In one embodiment, the chase buffer contains a tris base, sodium citrate, EDTA, casein, Tween-20™ surfactant, sodium azide, and sodium hydroxide or other suitable base to bring the pH of the chase buffer to about 8.3. The concentration of tris base may be between about 0.05 M to 1.5 M, or about 0.1 M. The sodium citrate and EDTA are each good chelating agents and each assists in chelating metals that may be a component of the dried labeled detection reagents which are specific for the analytes of interest, where the label may also be referred to as a reporter agent, and the label may be made from, e.g., gold. The concentration of sodium citrate may be between about 100 mM to about 400 mM, or about 300 mM. The concentration of EDTA may be between about 20 mM to about 40 mM, or about 30 mM. The concentration of casein may be about 0.5% to about 1.5%, or about 1% as measured by weight casein/volume buffer. Casein is an exemplary protein solution that may be used in the chase buffer, and functions as a blocking agent. Other blocking agents as known in the art may be used in lieu of, or in addition to, casein. The concentration of Tween-20™ surfactant may be about 0.05% to about 0.15%, or about 0.1% as measured by volume Tween-20/volume buffer. The Tween-20™ helps to wet out the sample application pad, which tends to be somewhat hydrophobic. Other surfactants and detergents may be used for the same purpose, with the concentration adjusted as needed to provide good wetting of the sample application pad. The concentration of the sodium azide should be effective to provide preservative efficacy for the buffer, where a suitable concentration is about 0.1% to about 0.3%, or about 0.2% as measured on a weight/volume basis.

In certain embodiments, the chase buffer comprises a buffer system such as phosphate, Tris-Cl, borate, bicarbonate, etc., mixed with a detergent such as Tween-20™, Triton X100™ or other non-ionic detergent, CHAPS, non-interfering protein or non-protein blocking substances, such as bovine serum albumin, gelatin or other animal serum- or milk-derived proteins, such as casein, and anti-microbial and anti-fungal substances, such as sodium azide. Considering the needs for product shelf life and ease of evaluation, phosphate based buffers may be preferred.

In one embodiment the chase buffer comprises two different chelating agents, one of the agents being a salt of a polyamine such as ethylenediamine, e.g., the tetraacetate salt of ethylenediamine (EDTA), and the other being a salt of a polycarboxylic organic acid such as citric acid, e.g., sodium citrate. By effectively chelating to the labeled detection reagents that were placed in the capture region of the capture membrane, the chase buffer carries all of the labeled detection reagents that are not bound to a test strip reagent, to the control region and optionally into the absorption pad. This effectively cleans up the appearance of the test region, removing some or all of the background color caused by residual labeled detection reagents in the test region. If the test region contains residual background color, that background color can interfere with the observer's ability to see a signal present on a test line. In addition to the two different chelating agents, a chase buffer of the present invention may contain buffering agents that maintain the buffer at a desired pH, such as tris base and sodium hydroxide, detergent (also referred to as surfactant), blocking agent and preservative, as well as other components.

The volume of chase buffer used will vary depending on the system, and may be between about 5-500 µl, for example between 10-100 µl or 100-200 µl or 200-300 µl, or 300-400 µl, or 400-500 µl.

The liquid test sample contacts each of the two labeled detection reagents at regions 28 and 30 where the labeled detection reagents are mixed and, if either of analytes X and Y is present in the test sample, labeled detection reagent-analyte conjugates are formed. The labeled detection reagent-analyte conjugates and non-conjugated labeled detection reagents then flow longitudinally through the device, with little to no perpendicular flow, such that individual assay test paths are formed for each of analytes X and Y. Once the flow reaches test lines 32 and 34, any labeled detection reagent-analyte conjugates bind to the capture reagents and become immobilized, resulting in detectable colored lines or rectangles at test lines 32 and 34. The non-conjugated labeled detection reagents continue to travel along the individual assay test paths and bind to, and are immobilized at, control line 26 resulting in a detectable colored line. If a colored line is not observed at control line 26, the test is considered invalid.

No physical barrier is required on the membrane between the individual labeled detection reagents or between the individual test lines to create a physical, separated, lane for each of the analyte assays, rather each assay test path is effectively separated from its neighboring assay test paths by the low diffusion constants of the labeled detection reagents.

When no physical barrier is present on the membrane between the individual labeled detection reagents, or between the individual test lines, then the two or more individual test lines may said to be located within a single region, which may also be referred to as a single assay chamber. The membrane has a capture region which is located directly adjacent to the sample receiving region, a test region which is directly adjacent to the capture region, and a control region which is directly adjacent to the test region. In various embodiments of the present disclosure, the area within a single assay chamber, which contains a capture region, a test region and a control region, contains two, or three, or four, or five, or six, or seven, or eight, or more than eight test lines, each test line running through the test region and portions of the capture region and control region. In this way, liquid sample does not need to be split and then directed into separate assay chambers, but instead the entire sample enters a single assay chamber and thereafter contacts multiple individual labeled detection reagents to thereby create multiple test lines within a single chamber. The two, three, four, five, six, seven, eight, or more individual labeled detection reagents are all located on a single sheet of nitrocellulose which is located in one assay chamber. In this way, a single assay chamber comprises both a first assay for detecting the presence of a first analyte in the liquid sample and a second assay for detecting the presence of a second analyte in the sample liquid sample, where optionally the first assay is performed on a first test line and the second assay is performed on a second test line, where the second test line is parallel to the first test line.

As no physical barrier is necessary to create the multiplexed lanes in the present device, the assay can also be performed in a "dipstick" format, i.e. a plastic enclosure or housing may or may not be used to perform the multiplexed assay. However, the inclusion of a housing may be preferred for certain applications.

A device of the present disclosure, including components thereof such as a test strip 21 of the present invention, has a proximal end and a distal end, where the flow direction of a test sample is from the proximal end to the distal end of the device, test strip or component thereof. When the observer looks down onto the test strip 21, the test strip 21 and components thereof have a left edge and a right edge, where the proximal end is closest to the observer and the distal end is furthest from the observer.

The buffer pad, hydrophobic pad and sample application pad may each be prepared from materials known in the art for use in making sample application pads, e.g., woven meshes and cellulose filters. Suitable materials are available from Ahlstrom Corporation (Helsinki, Finland), for example, their CytoSep® media may be used to form a buffer pad and/or a hydrophobic pad and/or a sample application pad. CytoSep® media has the property that it is a single layer media consisting of high purity natural and synthetic fibers, where the untreated media contains no chemical interfering substances and shows to significant binding of plasma components. CytoSep® media retains red blood cells while allowing serum to flow rapidly. In one embodiment the application pad is a cellulose filter.

A device or test strip of the present disclosure optionally comprises a backing card, which may also be referred to as a support card or support film. The backing card is preferably impermeable to water. The sample application pad and other features of the test strip may be adhered to the backing card. The backing card is rigid or semi-rigid so that the test strip maintains a flat shape. A primary purpose of the backing card is to make the test strip easier to handle. The backing card may be formed from materials known in the art for this purpose, e.g., plastic or mylar. Sometimes the skilled person refers to the backing card as a plastic card or a mylar card or an adhesive card.

The capture membrane of the present disclosure comprises one or more spots at the proximal end of the membrane, where those one or more spots contain dry labeled detection reagents that is or are specific for analyte(s) of interest. For example, in FIG. 3A, two spots 28 and 30 are shown. The capture membrane comprises one or more test lines located between the control line 26 and the spots 28 and 30 (by reference to FIG. 3A). Each test line contains an immobilized capture reagent that is specific for an analyte of interest. In FIG. 3A, two test lines 32 and 34 are shown.

A test strip that comprises a capture membrane of the present disclosure may have a reservoir region to soak up excess fluid. The reservoir region may comprise an absorbent pad, which is located at the distal end of the test strip shown. The primary function of the absorbent pad is to absorb the water and solubilized components present in the test sample and the chase buffer after they pass through the test lines and the control line. As the desired volume of test sample and/or chase buffer is increased, the holding capacity of the absorbent pad should likewise be increased. The volume of test sample used in the methods of the present disclosure may be at least 10 µL, or 20 µL, or 30 µL, or 40 µL, or 50 µL, or 60 µL, or 70 µL, or 80 µL, or 90 µL, or 100 µL, or 110 µL, or 120 µL, or 130 µL, or 140 µL, or 150 µL, or 160 µL, or 170 µL, or 180 µL, or 190 µL, and is typically less than 1,000 µL, or 900 µL, or 800 µL, or 700 µL, or 600 µL, or 500 µL, or 400 µL, or 300 µL, or 200 µL, or 100 µL, including ranges defined by any two of these values. For example, a volume of liquid test sample of 50-200 µL, or 50 to 150 µL, may be applied to the test sample receiving region.

A suitable absorbent pad may be prepared from, e.g., cellulose filters. The flow of liquid into the absorbent pad may not be laminar, which leads to uneven flow of the solvent front down the membrane. To address the consequences of a non-laminar flow, in one embodiment the test strips of the invention include an intermediate absorbent pad (shown as feature 40 in FIG. 3C) which is located between the absorbent pad and the distal end of the capture membrane. The intermediate absorbent pad may be more porous than is the absorbent pad, thereby allowing entering solvent to evenly distribute in a direction perpendicular to the flow of the solvent, i.e., the omega (Ω) direction. After passing through the intermediate absorbent pad, the solvent and dissolved components more evenly enter the absorbent pad, i.e., enter the absorbent pad with an enhanced laminar flow.

In use, the sample application pad can receive both the test sample and thereafter receive the chase buffer. However, in one embodiment of the test strip of the invention, a separate buffer pad is provided to receive the chase buffer. The buffer pad is located upstream of the application pad, at the proximal end of the test strip. The buffer pad may be made from the same materials that are used to prepare the application pad. However, by having the application pad separate from the buffer pad 38 it is possible to select different materials for the two different pads, and/or differentially treat the application pad and the buffer pad so that they have different properties.

The buffer pad may optionally be located directly next to the application pad or alternatively a hydrophobic pad may be positioned between the application pad and the buffer pad. In one embodiment the hydrophobic pad has a different hydrophobicity compared to the hydrophobicity of the application pad. In one embodiment the hydrophobic pad has a different hydrophobicity compared to the hydrophobicity of the buffer pad. In one embodiment, the hydrophobic pad is more hydrophobic compared to the hydrophobicity of each of the buffer pad and the application pad, i.e., the buffer pad and the application pad are each less hydrophobic than the hydrophobic pad. The relative hydrophobicity of two adjacent pads is readily determined by placing a dyed aqueous sample onto one or both of the adjacent pads: the aqueous sample will tend to migrate to the more hydrophilic paid, i.e., the less hydrophobic pad, all other factors being equal.

Figure 4B:
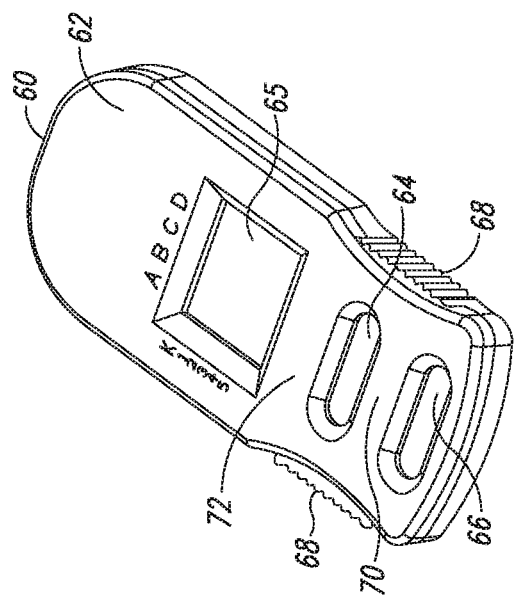
FIG. 4B shows a multiplex lateral flow assay device of the present disclosure enclosed in a plastic housing.
Figure 4A:
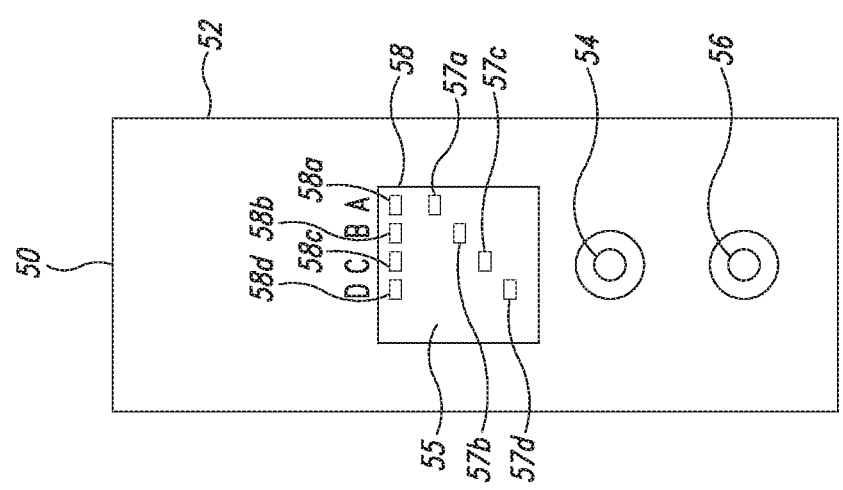
FIG. 4A shows a multiplex lateral flow assay device of the present disclosure enclosed in a plastic housing.

FIG. 4A shows a multiplex lateral flow assay device 50 of the present disclosure including a housing 52. Housing 52 is made of a generally rigid durable material, such as plastic. The term "generally rigid" as used herein in reference to the housing refers to a material which is sufficiently rigid to maintain the test strip in position relative to the other features of the device and signal detection system during use of the test device in a lateral flow assay method. Device 50 is testing for the presence of four different analytes within a single sample, each of the four different analytes being evaluated in one of assay paths A, B, C or D. Device 50 is provided with four test lines (not specifically shown). Device 50 includes a port 54 for application of the sample to be tested and a separate port 56 for application of a buffer. The device 50 can alternatively have a single port which is used for application of both the test sample and the buffer. Device 50 also includes a window 55 where the results of the assay are seen. FIG. 4A shows device 50 after it has been used to analyze a sample, where that sample contained four analytes, as indicated by the four visible rectangles 57a, 57b, 57c and 57d seen in the window 55. Device 50 includes a control line 58, the presence of which is seen by the appearance of four rectangles 58a, 58b, 58c and 58d in a single row within window 55.

FIG. 4B provides another illustration of a multiplex lateral flow assay device 60 of the present disclosure including a housing 62. Housing 62 is made of a generally rigid durable material, such as plastic. The housing 62 of device 60 identifies four assay test paths A, B, C and D. In addition, the housing 62 of device 60 identifies five test lines (1, 2, 3, 4 and 5). In addition, the housing 62 of device 60 identifies a control line (K). Device 60 includes a port 64 for application of the sample to be tested and a separate port 66 for application of a buffer. Those of skill in the art will appreciate that device 60 can alternatively have a single port which is used for application of both the test sample and the buffer. Device 60 also includes a window 65 where the results of the assay are seen and is shown with optional finger grips 68 on either side of the device 60. When a test strip of the present invention, such as illustrated in FIGS. 2A 2B, 3A and 3B, is placed within the housing 62, the sample pad 22 will be exposed through port 64 and the buffer pad 38 will be exposed through port 66. The hydrophobic pad 39 will lie below the region 70 of the housing 62 while the spots (e.g., 28 and 30) lie below the region 72 of the housing 62. FIG. 4B shows device 60 before it has been used to analyze a sample, and thus no signals are seen in the window 65.

Figure 5B:
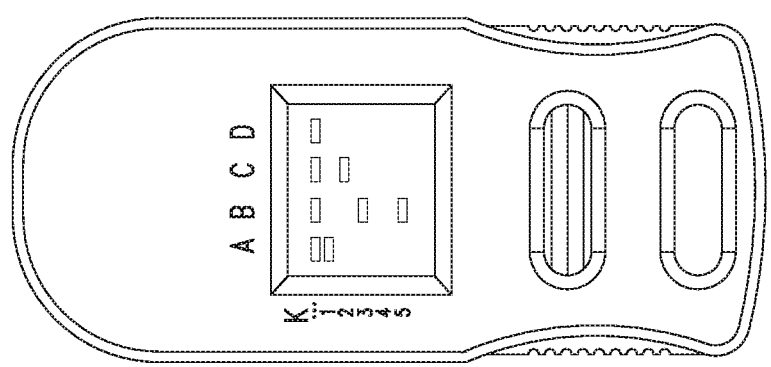
FIG. 5B shows the result of assaying a test sample in a device of the present disclosure, where the test sample contains four analytes of interest.
Figure 5A:
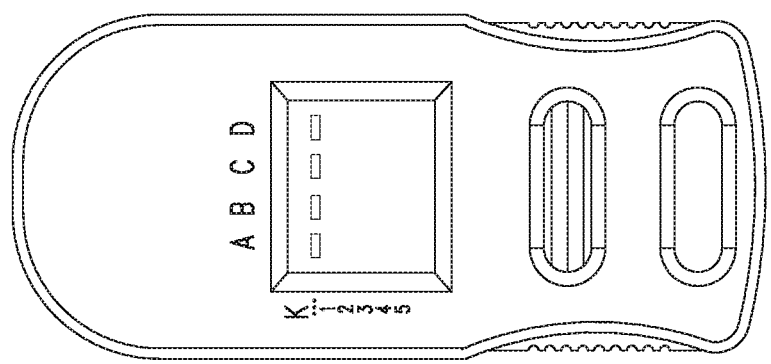
FIG. 5A shows the result of assaying a test sample in a device of the present disclosure, where the test sample does not contain any analytes of interest.

FIG. 5A and FIG. 5B show two identical rapid test devices of the present invention comprising a cassette and a test strip. The device of FIG. 5A has been used to analyze a first sample while the device of FIG. 5B has been used to analyze a second (different from the first) sample. Each rapid test device can detect the presence of the same four analytes as shown in the Interpretation Chart.

| | Interpretation Chart | | | |
|---|---|---|---|---|
| | A | B | C | D |
| K | A-control | B-control | C-control | D-control |
| 1 | A1 = Dengue (NS1) | * | * | * |
| 2 | * | * | C2 = Chikungunya (E1/E2 Protein) | * |
| 3 | * | B3 = Malaria (pfHRP2) | * | * |
| 4 | * | * | * | * |
| 5 | * | B5 = Melioidosis (CPS) | * | * |

*If any signal appears here, the signal may be ignored since it is due to non-specific interactions.

The test device shown in FIG. 5A has four rectangles in the window, providing a signal in each of assay test paths A, B, C and D in the control line K only. Accordingly, the person from whom the sample was taken and tested with the device of FIG. 5A did not have any of the diseases dengue, malaria, melioidosis or chikungunya. In contrast, the test device shown in FIG. 5B has eight rectangles in the window, providing a signal in each of assay test paths A, B, C and D in the control line K, and additionally providing signals at locations A-1, B-3, B-5 and C-2. Accordingly, the person from whom the sample was taken and tested with the device of FIG. 5B does have each of the diseases dengue, malaria, melioidosis or chikungunya.

In other embodiments the present disclosure provides methods for detecting the presence of one or more analytes of interest, e.g., a plurality of analytes of interest, in a liquid test sample. In certain embodiments, these methods comprise providing a multiplex lateral flow assay device as described herein, e.g., a multiplex lateral flow assay device which comprises a sample receiving region, where the sample receiving region comprises a sample application pad. The sample receiving region is adjacent to a capture membrane, where aqueous liquid can flow from the pad and into the membrane. The capture membrane, which may also be referred to as a capillary membrane or an analytical membrane, comprises three regions: a capture region which is located directly adjacent to the sample receiving region, a test region which is directly adjacent to the capture region, and a control region which is directly adjacent to the test region. When liquid test sample is placed in the sample receiving region, most or all of that liquid flows in the downstream theta (Θ) direction, passing from the sample application pad into the capture region of the membrane, and from the capture region into the test region of the membrane, and from test region into the control region of the capture membrane.

The capture region of the capture membrane comprises one more spots, e.g., 1 spot, 2 spots, 3 spots, 4 spots, 5 spots, 6, spots, 7 spots, 8 spots, 9 spots, 10 spots, etc. Within each spot is located one or more unique immobilized labelled detection reagents. A unique immobilized labelled detection reagent is specific for a unique analyte of interest in the liquid test sample. A labelled detection reagent comprises a detection reagent, e.g., an antibody or an antigen, which is specific for, e.g., specifically reacts with, an analyte of interest that may be present in the liquid test sample, where the detection reagent is stably joined to a reporter agent, e.g., a gold particle.

When liquid test sample leaves the sample receiving region and enters the capture region, the liquid test sample will contact the immobilized labelled detection reagents in each of the spots in the capture region, and then will continue flowing longitudinally, i.e., in the downstream direction, from the spots towards the control region 82. During this downstream travel, the liquid test sample, which has optionally reacted with labelled detection reagent, will define an assay test path. For example, a first assay test path is defined as beginning at and including the spot and ending at distal end of the capture membrane, the first test path being a straight or substantially straight line which is the shortest distance between the spot and the distal end of the capture membrane. Likewise, a second assay test path is defined as beginning at and including a second different spot laterally displaced from the first spot and ending at distal end of the capture membrane, the second test path being a straight or substantially straight line which is the shortest distance between the second spot and the distal end of the capture membrane. Each of the first and second labelled detection reagents preferably has a low diffusion constant such that there is little or no lateral diffusion of the first and second labeled detection reagents between the first and second assay test path following solubilization by the liquid test sample.

The test region comprises one or more test lines, where a test line may extend completely or partially across the membrane. Within a first test line is located an immobilized first capture reagent specific for the first analyte of interest. Within second test line is located an immobilized second (different from the first) capture reagent specific for the second analyte of interest.

Methods of the invention may include allowing the labeled detection reagent-analytes to migrate through the capture membrane, with each labeled detection reagent-analyte migrating along a specific assay test path to a test line that is specific for the specific analyte, wherein formation of a detectable signal at a specific test line is indicative of the presence of the specific analyte in the sample. For example, if the test sample contains a first analyte of interest, then when that test sample migrates from the sample receiving region and enters the first spot, the first analyte of interest will react with the first immobilized labelled detection reagent to form a first labeled detection reagent-analyte which becomes solubilized and leaves the first spot and travels along the first assay test path until it contacts the first test line which contains a first immobilized capture reagent. Upon reaching the first test line, the first labeled detection reagent-analyte will react with the first immobilized capture reagent and remain fixed at the location of reaction. The reporter agent which originated with the labeled detection reagent thus becomes immobilized along the first assay path at the location of the first test line. The reporter agent can be visualized by the observer, and thus the observer gains The methods of the present invention optionally include applying a chase buffer to the sample receiving region. The chase buffer is applied after the test sample is deposited on the application pad, and preferably after the test sample has traveled past one or more of the test lines. The chase buffer assures that all of the labeled detection reagent-analyte travels to one or more test lines and then to the control region, so long as the labeled detection reagent-analyte has not reacted with a capture reagent in a test line. The chase buffer thus assure a clean background in the test region and the control region.

Alternatively, the chase buffer may be deposited on a buffer pad that is upstream from the sample application pad. The buffer pad absorbs the chase buffer and then releases the chase buffer to the application pad located in the sample receiving region. In an alternative embodiment, a hydrophobic pad is located between the buffer pad and the sample receiving pad. The hydrophobic pad 104 provides a delayed flow of chase buffer from the buffer pad to the sample receiving pad because the hydrophobic pad is more hydrophobic than either of the buffer pad or the application pad. Because of the relatively more hydrophobic nature of the hydrophobic pad compared to the hydrophobicity of the application pad and the capture membrane, when aqueous test sample is added to the application pad, that aqueous test sample will preferentially move into the capture membrane rather than into the hydrophobic pad or the buffer pad. Because of the relatively more hydrophobic nature of the hydrophobic pad compared to the hydrophobicity of the buffer pad, when the chase buffer is added to the buffer pad, that chase buffer will not quickly migrate into the hydrophobic pad or the application pad. However, the chase buffer will gradually migrate through the hydrophobic pad and then into application pad prior to entering the capture membrane.

The somewhat retarded or delayed migration of chase buffer from the buffer pad into the capture membrane, caused by the relatively high hydrophobicity of the hydrophobic pad, contributes to a uniform solvent front of chase buffer as the chase buffer enters and travels through the capture membrane. The uniform solvent front assists in maintaining reagents in narrow assay test paths that do not overlap with one another, thus leading to clearer and more reliable readings.

The user of the test strip of the invention may add chase buffer to the chase buffer pad immediately after adding test sample to the sample application pad. Because of the hydrophobic nature of the intervening hydrophobic pad, the chase buffer only slowly migrates to the capture membrane, effectively creating a delayed addition of the chase buffer to the capture membrane even though the chase buffer is added to the test strip immediately after the test sample is added to the test strip. This delay in contact between the chase buffer and the capture membrane due to the presence of the hydrophobic pad provides added convenience for the user of the device of the present disclosure because the user does not need to wait a suitable time, e.g., a few minutes, before adding the chase buffer to the device.

The following are additional exemplary embodiments of the present disclosure:

1) A multiplex lateral flow assay device for simultaneous detection of a presence of at least a first analyte of interest and a second, different, analyte of interest in a single liquid test sample, comprising:
a. a test sample receiving region; and
b. a capture membrane comprising a first assay test path and a second, adjacent, assay test path, the first assay test path comprising a first labeled detection reagent specific for the first analyte of interest, and a first test line comprising an immobilized first capture reagent specific for the first analyte of interest, and the second assay test path comprising a second, different, labeled detection reagent specific for the second analyte of interest, and a second test line comprising an immobilized second, different, capture reagent specific for the second analyte of interest. The capture membrane is a single, i.e., a continuous, piece of material on which the first and second, and optionally additional assay test paths are located. The entire first and second assay test paths, and optionally additional assay test paths, are located within a single, i.e., the same, assay chamber 2) The device of embodiment 1, wherein each of the first and second labeled detection reagents has a low diffusion constant such that there is little to no lateral diffusion of the first and second labeled detection reagents between the first and second assay test paths following solubilization by the liquid test sample.

3) The device of embodiments 1 and 2, wherein the first and second labeled detection reagents are in dry form on the capture membrane, and the capture membrane is formed from nitrocellulose.

4) The device of any of embodiments 1-3, wherein at least one of the first and second labeled detection reagents comprises a reporter agent selected from the group consisting of: colloidal nanoparticles, latex microspheres, quantum dots, enzymes and fluorophores.

5) The device of embodiment 4, wherein the reporter agent comprises gold nanoparticle.

6) The device of any of embodiments 1-5, wherein the first labeled detection reagent and the second labeled detection reagent are each geographically localized in first and second spots, respectively, and each of the first and second spots further comprises a water-soluble non-volatile organic molecule.

7) The device of embodiment 6, wherein the water-soluble non-volatile organic molecule is independently at each occurrence selected from the group consisting of disaccharide, polyvinylalcohol (PVA) and polyhydric nonionic surfactant.

8) The device of any of embodiments 1-7, wherein the first assay test path comprises a third labeled detection reagent in dry form on the capture membrane that is specific for a third analyte of interest, and further comprises a third test line comprising a third immobilized capture reagent specific for the third analyte of interest.

9) The device of any of embodiments 1-8, wherein the device lacks physical or chemical barriers between the first and the second assay test paths.

10) The device of any of embodiments 1-9, wherein the first test line extends continuously across the capture membrane and intersects with each assay path of the capture membrane.

11) The device of any of embodiments 1-10, further comprising a control line positioned downstream of the first and second test lines, the control line comprising an immobilized control reagent that binds to the first and second labeled detection reagents.

12) The device of any of embodiments 1-11, further comprising a reservoir region positioned downstream of the capture membrane for absorbing an excess of liquid.

13) The device of embodiment 12, wherein the reservoir region comprises an absorbent pad, and further comprises an intermediate pad located between the capture membrane and the absorbent pad, where the intermediate pad is water-absorbent and is more hydrophilic than the absorbent pad.

14) The device of any of embodiments 1-13, wherein the test sample receiving region comprises a test sample application pad, the test sample receiving region further comprising a buffer pad and a hydrophobic pad, each of the application pad, buffer pad and hydrophobic pad being formed from porous, water-absorbing material, the hydrophobic pad located adjacent to and upstream from the application pad, the buffer pad located adjacent to and upstream from the hydrophobic pad, where the hydrophobic pad is more hydrophobic than either of the buffer pad or the application pad.

15) A kit comprising the device of any of embodiments 1-14 and instructions for its use.

16) A method for detecting the presence of a first analyte of interest and a second, different, analyte of interest in a liquid test sample, comprising:
a. providing a multiplex lateral flow assay device of embodiment 1;
b. applying the liquid test sample to the test sample receiving region;
c. allowing the liquid test sample to contact the first and second labeled detection reagents, whereby labeled detection reagent-analyte conjugates are formed if one or more of the first and second analytes is present in the sample; and
d. allowing the labeled detection reagent-analyte conjugates to migrate through the capture membrane along the first and second assay test paths to the first and second test lines,
wherein formation of a detectable signal at the first and/or second test lines is indicative of the presence of the first and/or second analytes in the liquid test samples.

17) The method of embodiment 16, further comprising applying a volume of chase buffer to the test sample receiving region after step b).

18) The method of embodiments 16 or 17, wherein the liquid test sample is a biological sample.

19) The method of any of embodiments 16-18, wherein the first analyte is a first antigen or antibody specific for a first infectious disease and the second analyte is a second antigen or antibody specific for a second, different, infectious disease.

20) The method of embodiment 19, wherein the first and second infectious diseases are each selected from the group consisting of: malaria, scrub typhus, rickettsia, typhoid fever, dengue, chikungunya, melioidosis, anthrax, and plague, leishmaniasis, tuberculosis, syphilis, Chagas disease, encephalitis, leprosy, West Nile virus, Shigella, *Campylobacter*, and enterotoxigenic *E. coli*.

All of the features disclosed in this specification may be combined in any combination. Thus, unless expressly stated otherwise, each feature disclosed is only an example of a generic series of equivalent or similar features. For example, in any of the devices, methods or kits of the present disclosure, a first analyte may be a first antigen or antibody specific for a first infectious disease and the second analyte may be a second antigen or antibody specific for a second, different, infectious disease. In addition, the first and second infectious diseases are each optionally selected from any one or more of malaria, scrub typhus, rickettsia, typhoid fever, dengue, chikungunya, melioidosis, anthrax, plague, leishmaniasis, tuberculosis, syphilis, Chagas disease, encephalitis, leprosy, West Nile virus, Shigella, *Campylobacter*, and enterotoxigenic *E. coli*.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended, and those skilled in the art will recognize, that the invention embraces and is also thereby described in terms of any individual member and any subgroup of members of the Markush group, and Applicants reserve the right to revise the application or claims to refer specifically to any individual member or any subgroup of members of the Markush group.

The following Examples are offered by way of illustration and not by way of limitation.

Example

Detection of Four Different Disorders Simultaneously Using a Multiplex Immunoassay The ability of a multiplex immunoassay of the present disclosure to detect the presence of chikungunya, dengue, malaria, and melioidosis antigens in a human serum sample was examined as follows.

Figure 6A:
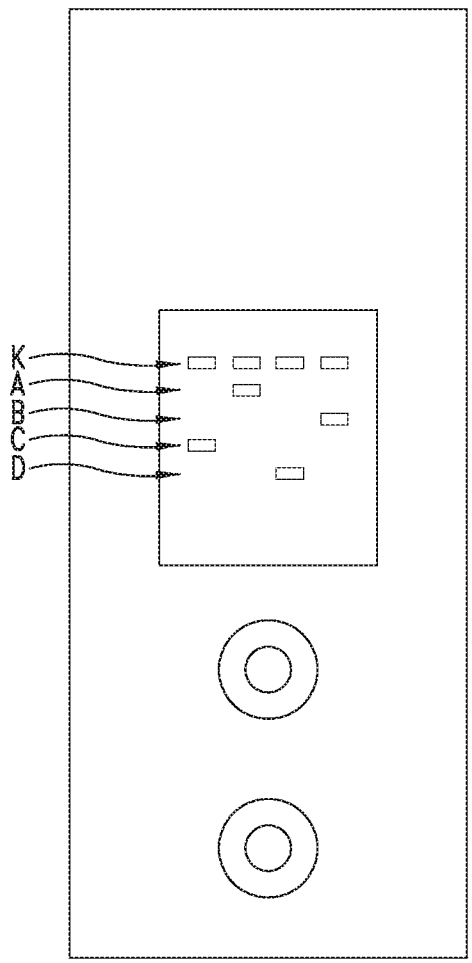
FIG. 6A shows the results of the evaluation of a single (spiked) specimen for four different target molecules simultaneously using a multiplex lateral flow assay device of the present disclosure.
Figure 6B:
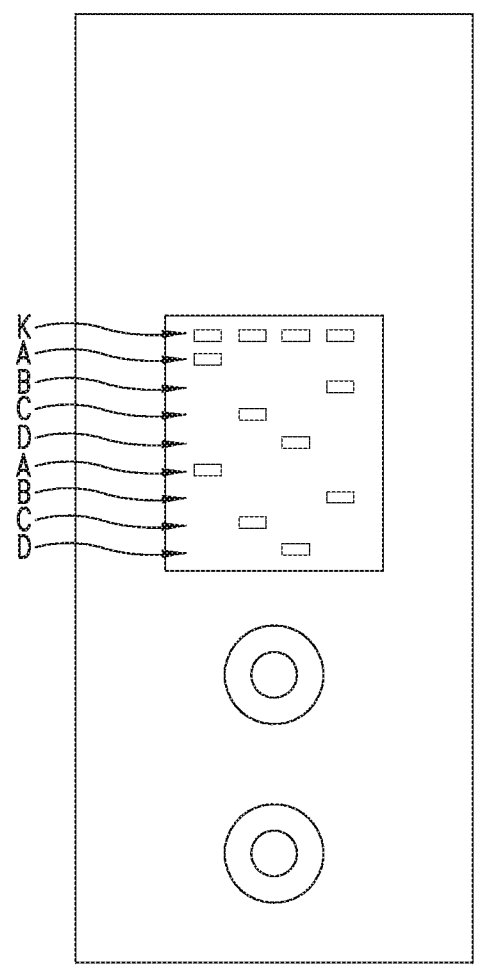
FIG. 6B shows an example of a multiplex lateral flow assay device of the present disclosure wherein multiple detector reagents are present in each lane.

Antibodies against chikungunya, dengue, malaria and melioidosis were labeled with 40 nm diameter gold nanoparticles, and individually spotted directly onto a Millipore HF135 nitrocellulose membrane of a lateral flow assay device between the sample pad and the test lines, with each of the labeled antibodies being positioned in a different region generally perpendicular to the elongated edges of the nitrocellulose pad. Four test lines were sprayed onto the membrane as follows, as illustrated in FIG. 6A and FIG. 6B:

A. Chk 1 75 @ 0.85 mg/ml [CHIKUNGUNYA antigen]

B. NS1 antibody v2 @ 3.5 mg/ml total [DENGUE; NS1 antigen]

C. Malaria anti-HRP-2 antibody @ 1.5 mg/ml [MALARIA; HRP2 antigen]

D. 4C4 @ 0.75 mg/ml [MELIOIDOSIS; CPS antigen]

Following application of the labeled antibodies, test lines and control line, the device was sealed in a plastic housing including a sample port and a buffer port.

100 ng of each of the respective chikungunya (A), dengue (B; NS1 antigen), malaria (C; HRP2 antigen) and melioidosis (D; CPS antigen) antigens was diluted into a normal human serum sample. The sample was then added to the sample port of the device after which approximately 2 drops of chase buffer were placed in the buffer port and the results were read approximately 20 minutes later. As shown in FIG. 6A, the assay shows the presence of all four antigens (A, B, C and D) within the test sample. Location K is the control line.

FIG. 6B shows the results of an assay in which multiple labeled detection reagents were spotted in each "lane" or assay test path of the device, with the additional test lines being the same as the four test lines in the device of FIG. 6A, repeated in the same order. These results demonstrate that each "lane" or assay test path can be used to evaluate two or more independent analytes, effectively multiplying the number of binding pair events that can be detected in the assay.

All references disclosed herein, including patent references and non-patent references, are hereby incorporated by reference in their entirety as if each was incorporated individually.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include", as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the presently described invention. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

What is claimed is:

1. A multiplex lateral flow assay device for simultaneous detection of a presence of at least a first analyte of interest and a second, different, analyte of interest in a single liquid test sample, comprising:
    a) a test sample receiving region; and
    b) a capture membrane comprising a first assay test path and a second, adjacent, assay test path, the first assay test path comprising a first labeled detection reagent specific for the first analyte of interest, and a first test line comprising an immobilized first capture reagent specific for the first analyte of interest, and the second assay test path comprising a second, different, labeled detection reagent specific for the second analyte of interest, and a second test line comprising an immobilized second, different, capture reagent specific for the second analyte of interest;
    wherein the device lacks physical or chemical barriers between the first and the second assay test paths; and
    wherein each of the first and second labeled detection reagents has a diffusion constant of less than $10^{-8}$ $m^2$/sec, such that there is little to no lateral diffusion of the first and second labeled detection reagents between the first and second assay test paths following solubilization by the liquid test sample.

2. The device of claim 1, wherein the first and second labeled detection reagents are in dry form on the capture membrane, and the capture membrane is formed from nitrocellulose.

3. The device of claim 1, wherein at least one of the first and second labeled detection reagents comprises a reporter agent selected from the group consisting of: colloidal nanoparticles, latex microspheres, quantum dots, enzymes and fluorophores.

4. The device of claim 3, wherein the reporter agent comprises gold nanoparticle.

5. The device of claim 1, wherein the first labeled detection reagent and the second labeled detection reagent are each geographically localized in first and second spots, respectively, and each of the first and second spots further comprises a water-soluble non-volatile organic molecule.

6. The device of claim 5, wherein the water-soluble non-volatile organic molecule is independently at each occurrence selected from the group consisting of disaccharide, polyvinylalcohol (PVA) and polyhydric nonionic surfactant.

7. The device of claim 1, further comprising a control line positioned downstream of the first and second test lines, the control line comprising an immobilized control reagent that binds to the first and second labeled detection reagents.

8. A kit comprising the device of claim 1, and instructions for its use.

9. A method for detecting the presence of a first analyte of interest and a second, different, analyte of interest in a liquid test sample, comprising:
 a) providing a multiplex lateral flow assay device of claim 1;
 b) applying the liquid test sample to the test sample receiving region;
 c) allowing the liquid test sample to contact the first and second labeled detection reagents, whereby labeled detection reagent-analyte conjugates are formed if one or more of the first and second analytes is present in the sample; and
 d) allowing the labeled detection reagent-analyte conjugates to migrate through the capture membrane along the first and second assay test paths to the first and second test lines,
 wherein formation of a detectable signal at the first and/or second test lines is indicative of the presence of the first and/or second analytes in the liquid test samples.

10. The method of claim 9, further comprising applying a volume of chase buffer to the test sample receiving region after step b).

11. The method of claim 9, wherein the liquid test sample is a biological sample.

12. The method of claim 9, wherein the first analyte is a first antigen or antibody specific for a first infectious disease and the second analyte is a second antigen or antibody specific for a second, different, infectious disease.

13. The method of claim 12, wherein the first and second infectious diseases are each selected from the group consisting of: malaria, scrub typhus, *rickettsia*, typhoid fever, dengue, chikungunya, melioidosis, anthrax, and plague, leishmaniasis, tuberculosis, syphilis, Chagas disease, encephalitis, leprosy, West Nile virus, *Shigella*, *Campylobacter*, and enterotoxigenic *E. coli*.

14. A multiplex lateral flow assay device for simultaneous detection of a presence of at least a first analyte of interest and a second, different, analyte of interest in a single liquid test sample, comprising:
 a) a test sample receiving region; and
 b) a capture membrane comprising a first assay test path and a second, adjacent, assay test path, the first assay test path comprising a first labeled detection reagent specific for the first analyte of interest, and a first test line comprising an immobilized first capture reagent specific for the first analyte of interest, and the second assay test path comprising a second, different, labeled detection reagent specific for the second analyte of interest, and a second test line comprising an immobilized second, different, capture reagent specific for the second analyte of interest;
 wherein the device lacks physical or chemical barriers between the first and the second assay test paths; and
 wherein the first assay test path comprises a third labeled detection reagent in dry form on the capture membrane that is specific for a third analyte of interest, and further comprises a third test line comprising a third immobilized capture reagent specific for the third analyte of interest.

15. A kit comprising the device of claim 14 and instructions for its use.

16. A method for detecting the presence of a first analyte of interest and a second, different, analyte of interest in a liquid test sample, comprising:
 a) providing a multiplex lateral flow assay device of claim 14;
 b) applying the liquid test sample to the test sample receiving region;
 c) allowing the liquid test sample to contact the first and second labeled detection reagents, whereby labeled detection reagent-analyte conjugates are formed if one or more of the first and second analytes is present in the sample; and
 d) allowing the labeled detection reagent-analyte conjugates to migrate through the capture membrane along the first and second assay test paths to the first and second test lines,
 wherein formation of a detectable signal at the first and/or second test lines is indicative of the presence of the first and/or second analytes in the liquid test samples.

17. The method of claim 16, further comprising applying a volume of chase buffer to the test sample receiving region after step b).

18. The method of claim 16, wherein the liquid test sample is a biological sample.

19. The method of claim 16, wherein the first analyte is a first antigen or antibody specific for a first infectious disease and the second analyte is a second antigen or antibody specific for a second, different, infectious disease.

20. The method of claim 19, wherein the first and second infectious diseases are each selected from the group consisting of: malaria, scrub typhus, *rickettsia*, typhoid fever, dengue, chikungunya, melioidosis, anthrax, and plague, leishmaniasis, tuberculosis, syphilis, Chagas disease, encephalitis, leprosy, West Nile virus, *Shigella*, *Campylobacter*, and enterotoxigenic *E. coli*.

21. A multiplex lateral flow assay device for simultaneous detection of a presence of at least a first analyte of interest and a second, different, analyte of interest in a single liquid test sample, comprising:
 a) a test sample receiving region; and
 b) a capture membrane comprising a first assay test path and a second, adjacent, assay test path, the first assay test path comprising a first labeled detection reagent specific for the first analyte of interest, and a first test line comprising an immobilized first capture reagent specific for the first analyte of interest, and the second assay test path comprising a second, different, labeled detection reagent specific for the second analyte of interest, and a second test line comprising an immobilized second, different, capture reagent specific for the second analyte of interest;
 wherein the device lacks physical or chemical barriers between the first and the second assay test paths; and
 wherein the test sample receiving region comprises a test sample application pad, the test sample receiving region further comprising a buffer pad and a hydrophobic pad, each of the application pad, buffer pad and hydrophobic pad being formed from porous, water-absorbing material, the hydrophobic pad located adjacent to and upstream from the application pad, the buffer pad located adjacent to and upstream from the hydrophobic pad, where the hydrophobic pad is more hydrophobic than either of the buffer pad or the application pad.

22. A kit comprising the device of claim 21 and instructions for its use.

23. A method for detecting the presence of a first analyte of interest and a second, different, analyte of interest in a liquid test sample, comprising:
 a) providing a multiplex lateral flow assay device of claim 21;

b) applying the liquid test sample to the test sample receiving region;

c) allowing the liquid test sample to contact the first and second labeled detection reagents, whereby labeled detection reagent-analyte conjugates are formed if one or more of the first and second analytes is present in the sample; and d) allowing the labeled detection reagent-analyte conjugates to migrate through the capture membrane along the first and second assay test paths to the first and second test lines, wherein formation of a detectable signal at the first and/or second test lines is indicative of the presence of the first and/or second analytes in the liquid test samples.

24. The method of claim 23, further comprising applying a volume of chase buffer to the test sample receiving region after step b).

25. The method of claim 23, wherein the liquid test sample is a biological sample.

26. The method of claim 23, wherein the first analyte is a first antigen or antibody specific for a first infectious disease and the second analyte is a second antigen or antibody specific for a second, different, infectious disease.

27. The method of claim 26, wherein the first and second infectious diseases are each selected from the group consisting of: malaria, scrub typhus, *rickettsia*, typhoid fever, dengue, chikungunya, melioidosis, anthrax, and plague, leishmaniasis, tuberculosis, syphilis, Chagas disease, encephalitis, leprosy, West Nile virus, *Shigella*, *Campylobacter*, and enterotoxigenic *E. coli*.

28. A multiplex lateral flow assay device for simultaneous detection of a presence of at least a first analyte of interest and a second, different, analyte of interest in a single liquid test sample, comprising:

a) a test sample receiving region; and b) a capture membrane comprising a first assay test path and a second, adjacent, assay test path, the first assay test path comprising a first labeled detection reagent specific for the first analyte of interest, and a first test line comprising an immobilized first capture reagent specific for the first analyte of interest, and the second assay test path comprising a second, different, labeled detection reagent specific for the second analyte of interest, and a second test line comprising an immobilized second, different, capture reagent specific for the second analyte of interest;

wherein the first test line extends continuously across the capture membrane and intersects with each assay test path of the capture membrane.

29. A kit comprising the device of claim 28 and instructions for its use.

30. A method for detecting the presence of a first analyte of interest and a second, different, analyte of interest in a liquid test sample, comprising:

a) providing a multiplex lateral flow assay device of claim 28;

b) applying the liquid test sample to the test sample receiving region;

c) allowing the liquid test sample to contact the first and second labeled detection reagents, whereby labeled detection reagent-analyte conjugates are formed if one or more of the first and second analytes is present in the sample; and d) allowing the labeled detection reagent-analyte conjugates to migrate through the capture membrane along the first and second assay test paths to the first and second test lines, wherein formation of a detectable signal at the first and/or second test lines is indicative of the presence of the first and/or second analytes in the liquid test samples.

31. The method of claim 30, further comprising applying a volume of chase buffer to the test sample receiving region after step b).

32. The method of claim 30, wherein the liquid test sample is a biological sample.

33. The method of claim 30, wherein the first analyte is a first antigen or antibody specific for a first infectious disease and the second analyte is a second antigen or antibody specific for a second, different, infectious disease.

34. The method of claim 33, wherein the first and second infectious diseases are each selected from the group consisting of: malaria, scrub typhus, *rickettsia*, typhoid fever, dengue, chikungunya, melioidosis, anthrax, and plague, leishmaniasis, tuberculosis, syphilis, Chagas disease, encephalitis, leprosy, West Nile virus, *Shigella*, *Campylobacter*, and enterotoxigenic *E. coli*.

* * * * *